(12) United States Patent
Jacobsen et al.

(10) Patent No.: US 9,226,688 B2
(45) Date of Patent: Jan. 5, 2016

(54) FLEXIBLE CIRCUIT ASSEMBLIES

(71) Applicant: Medtronic Xomed, Inc., Jacksonville, FL (US)

(72) Inventors: Brad Jacobsen, Erie, CO (US); Bruce M. Burg, Louisville, CO (US); Abhishek Jain, Centennial, CO (US); Andrew Bzostek, Boulder, CO (US)

(73) Assignee: MEDTRONIC XOMED, INC., Jacksonville, FL (US)

( * ) Notice: Subject to any disclaimer, the term of this patent is extended or adjusted under 35 U.S.C. 154(b) by 154 days.

(21) Appl. No.: 13/748,150

(22) Filed: Jan. 23, 2013

(65) Prior Publication Data

US 2013/0137954 A1 May 30, 2013

Related U.S. Application Data

(63) Continuation-in-part of application No. 13/097,243, filed on Apr. 29, 2011, and a continuation-in-part of application No. 12/400,951, filed on Mar. 10, 2009, now Pat. No. 8,504,139.

(60) Provisional application No. 61/330,024, filed on Apr. 30, 2010.

(51) Int. Cl.
*A61B 5/055* (2006.01)
*A61B 5/06* (2006.01)
(Continued)

(52) U.S. Cl.
CPC ............. *A61B 5/065* (2013.01); *A61B 19/5244* (2013.01); *H05K 1/028* (2013.01);
(Continued)

(58) Field of Classification Search
CPC .................. A61B 5/065; A61B 17/24; A61B 2017/00946; A61B 19/5244; A61B 2019/547; A61B 2019/5483; A61B 2019/5251; H05K 1/0298; H05K 1/028; A61M 1/008; A61M 2205/3561; A61M 2205/3576
USPC .......................................................... 600/424
See application file for complete search history.

(56) References Cited

U.S. PATENT DOCUMENTS 4,317,078 A   2/1982   Weed et al.
4,788,987 A   12/1988  Nickel
(Continued)

FOREIGN PATENT DOCUMENTS

AU   2011245296 A1   12/2012
CA      2797359 A1   11/2011
(Continued)

OTHER PUBLICATIONS

"InstaTrak 3500 Plus. Applications: ENT. Cranial." http://www.gehealthcare/usen/xr/surgery/products/nay.html (printed Dec. 14, 2009).
(Continued)

*Primary Examiner* — Long V Le
*Assistant Examiner* — Angela M Hoffa
(74) *Attorney, Agent, or Firm* — Harness, Dickey

(57) ABSTRACT

A flexible circuit assembly can include a base layer, a plurality of circuit traces and an insulative layer. The plurality of circuit traces can each be coupled to a pair of circuit pads, and the circuit traces can be formed on an upper side of the base layer. The insulative layer can be formed over the circuit traces to isolate the circuit traces from an external environment. The base layer, plurality of circuit traces and insulative layer can form a flexible circuit sheet. The base layer and the insulative layer can include material properties and a thickness configured to facilitate the flexible circuit sheet being flexible such that the flexible circuit sheet is adapted to conform to a non-planar surface of the medical device.

26 Claims, 13 Drawing Sheets

(51) Int. Cl.
*H05K 1/02* (2006.01)
*A61B 19/00* (2006.01)
*A61M 1/00* (2006.01)
*A61B 17/24* (2006.01)
*A61B 17/00* (2006.01)

(52) U.S. Cl.
CPC .............. *H05K 1/0298* (2013.01); *A61B 17/24* (2013.01); *A61B 2017/00946* (2013.01); *A61B 2019/5251* (2013.01); *A61B 2019/547* (2013.01); *A61B 2019/5483* (2013.01); *A61M 1/008* (2013.01); *A61M 2205/3561* (2013.01); *A61M 2205/3576* (2013.01)

(56) References Cited

U.S. PATENT DOCUMENTS

| | | | |
|---|---|---|---|
| 4,806,182 | A | 2/1989 | Rydell et al. |
| 5,005,592 | A | 4/1991 | Cartmell |
| 5,226,423 | A | 7/1993 | Tenerz et al. |
| 5,391,199 | A | 2/1995 | Ben-Haim |
| 5,443,489 | A | 8/1995 | Ben-Haim |
| 5,591,141 | A | 1/1997 | Nettekoven |
| 5,592,939 | A | 1/1997 | Martinelli |
| 5,740,808 | A | 4/1998 | Panescu et al. |
| 5,762,637 | A | 6/1998 | Berg et al. |
| 5,840,024 | A | 11/1998 | Taniguchi et al. |
| 5,913,820 | A | 6/1999 | Bladen et al. |
| 5,938,602 | A | 8/1999 | Lloyd |
| 5,963,120 | A | 10/1999 | Zaviska |
| 5,983,126 | A | 11/1999 | Wittkampf |
| 6,021,343 | A | 2/2000 | Foley et al. |
| 6,106,486 | A | 8/2000 | Tenerz et al. |
| 6,201,387 | B1 | 3/2001 | Govari |
| 6,235,038 | B1 | 5/2001 | Hunter et al. |
| 6,253,770 | B1 | 7/2001 | Acker et al. |
| 6,254,600 | B1 | 7/2001 | Willink et al. |
| 6,332,891 | B1 | 12/2001 | Himes |
| 6,336,906 | B1 | 1/2002 | Hammarstrom et al. |
| 6,348,058 | B1 | 2/2002 | Melkent et al. |
| 6,381,485 | B1 | 4/2002 | Hunter et al. |
| 6,427,079 | B1 | 7/2002 | Schneider et al. |
| 6,434,507 | B1 | 8/2002 | Clayton et al. |
| 6,474,341 | B1 | 11/2002 | Hunter et al. |
| 6,478,802 | B2 | 11/2002 | Kienzle, III et al. |
| 6,556,857 | B1 | 4/2003 | Estes et al. |
| 6,610,066 | B2 | 8/2003 | Dinger et al. |
| 6,615,155 | B2 | 9/2003 | Gilboa |
| 6,616,651 | B1 | 9/2003 | Stevens |
| 6,687,531 | B1 | 2/2004 | Ferre et al. |
| 6,689,049 | B1 | 2/2004 | Miyagi et al. |
| 6,695,764 | B2 | 2/2004 | Silverman et al. |
| 6,747,539 | B1 | 6/2004 | Martinelli |
| 6,796,988 | B2 | 9/2004 | Estes et al. |
| 6,833,814 | B2 | 12/2004 | Gilboa et al. |
| 6,926,674 | B2 | 8/2005 | Tenerz et al. |
| 6,940,941 | B2 | 9/2005 | Gregerson et al. |
| 6,977,575 | B2 | 12/2005 | Bernier |
| 6,980,849 | B2 | 12/2005 | Sasso |
| 6,993,374 | B2 | 1/2006 | Sasso |
| 7,001,045 | B2 | 2/2006 | Gregerson et al. |
| 7,106,825 | B2 | 9/2006 | Gregerson et al. |
| 7,108,421 | B2 | 9/2006 | Gregerson et al. |
| 7,118,378 | B1 | 10/2006 | Karapetyan |
| 7,166,114 | B2 | 1/2007 | Moctezuma De La Barrera et al. |
| 7,188,998 | B2 | 3/2007 | Gregerson et al. |
| 7,226,456 | B2 | 6/2007 | O'Neil et al. |
| 7,346,417 | B2 | 3/2008 | Lüth et al. |
| 7,366,562 | B2 | 4/2008 | Dukesherer et al. |
| 7,410,480 | B2 | 8/2008 | Muni et al. |
| 7,462,175 | B2 | 12/2008 | Chang et al. |
| 7,500,971 | B2 | 3/2009 | Chang et al. |
| 7,537,594 | B2 | 5/2009 | Sartor |
| 7,559,137 | B2 | 7/2009 | Beer et al. |
| 7,604,609 | B2 | 10/2009 | Jervis |
| 7,625,617 | B1 | 12/2009 | Anderson et al. |
| 7,629,015 | B2 | 12/2009 | Anderson et al. |
| 7,637,896 | B2 | 12/2009 | Voegele et al. |
| 7,647,083 | B2 | 1/2010 | Al-Ali et al. |
| 7,697,972 | B2 | 4/2010 | Verard et al. |
| 7,751,865 | B2 | 7/2010 | Jascob et al. |
| 7,763,035 | B2 | 7/2010 | Melkent et al. |
| 7,774,933 | B2 | 8/2010 | Wilson et al. |
| 7,797,032 | B2 | 9/2010 | Martinelli et al. |
| 7,818,044 | B2 | 10/2010 | Dukesherer et al. |
| 7,840,253 | B2 | 11/2010 | Tremblay et al. |
| 7,844,319 | B2 | 11/2010 | Susil et al. |
| 7,971,341 | B2 | 7/2011 | Dukesherer et al. |
| 7,979,032 | B2 | 7/2011 | Lomnitz |
| 8,075,969 | B2 * | 12/2011 | Anderson et al. ............ 428/36.9 |
| 8,086,298 | B2 | 12/2011 | Whitmore, Iii et al. |
| 8,105,339 | B2 | 1/2012 | Melkent et al. |
| 8,147,486 | B2 * | 4/2012 | Honour et al. ................. 606/41 |
| 8,239,001 | B2 | 8/2012 | Verard et al. |
| 8,251,949 | B2 | 8/2012 | Warnack |
| 8,255,027 | B2 | 8/2012 | Al-Ali et al. |
| 8,504,139 | B2 | 8/2013 | Jacobsen et al. |
| 8,644,907 | B2 | 2/2014 | Hartmann et al. |
| 8,648,605 | B2 * | 2/2014 | Nakamura et al. ............ 324/464 |
| 8,674,694 | B2 | 3/2014 | Hyde et al. |
| 8,862,204 | B2 | 10/2014 | Sobe et al. |
| 2001/0034549 | A1 | 10/2001 | Bartholf et al. |
| 2002/0165448 | A1 | 11/2002 | Ben-Haim et al. |
| 2003/0050552 | A1 | 3/2003 | Vu |
| 2003/0187347 | A1 | 10/2003 | Nevo et al. |
| 2004/0116803 | A1 | 6/2004 | Jascob et al. |
| 2004/0199072 | A1 | 10/2004 | Sprouse et al. |
| 2004/0215071 | A1 | 10/2004 | Frank et al. |
| 2005/0027339 | A1 | 2/2005 | Schrom et al. |
| 2005/0027340 | A1 | 2/2005 | Schrom et al. |
| 2005/0027341 | A1 | 2/2005 | Schrom et al. |
| 2005/0060885 | A1 * | 3/2005 | Johnson et al. ................. 29/846 |
| 2005/0085715 | A1 | 4/2005 | Dukesherer et al. |
| 2005/0085720 | A1 | 4/2005 | Jascob et al. |
| 2005/0105212 | A1 | 5/2005 | Sato |
| 2005/0154294 | A1 | 7/2005 | Uchiyama et al. |
| 2005/0171508 | A1 | 8/2005 | Gilboa |
| 2005/0215922 | A1 | 9/2005 | Tsonton et al. |
| 2005/0222554 | A1 | 10/2005 | Wallace et al. |
| 2006/0004286 | A1 | 1/2006 | Chang et al. |
| 2006/0025677 | A1 | 2/2006 | Verard et al. |
| 2006/0036189 | A1 | 2/2006 | Martinelli et al. |
| 2006/0084867 | A1 | 4/2006 | Tremblay et al. |
| 2006/0142656 | A1 | 6/2006 | Malackowski et al. |
| 2006/0206039 | A1 | 9/2006 | Wilson et al. |
| 2006/0206170 | A1 | 9/2006 | Denker et al. |
| 2006/0224142 | A1 | 10/2006 | Wilson et al. |
| 2006/0229624 | A1 | 10/2006 | May et al. |
| 2006/0235314 | A1 | 10/2006 | Migliuolo et al. |
| 2007/0088416 | A1 * | 4/2007 | Atalar et al. .................. 607/115 |
| 2007/0157828 | A1 | 7/2007 | Susel et al. |
| 2007/0197899 | A1 | 8/2007 | Ritter et al. |
| 2007/0208252 | A1 | 9/2007 | Makower |
| 2007/0220746 | A1 | 9/2007 | Anderson et al. |
| 2007/0225595 | A1 | 9/2007 | Malackowski et al. |
| 2007/0255132 | A1 | 11/2007 | Shalgi et al. |
| 2008/0097195 | A1 | 4/2008 | Urquhart et al. |
| 2008/0097347 | A1 | 4/2008 | Arvanaghi |
| 2008/0119727 | A1 | 5/2008 | Barbagli et al. |
| 2008/0119919 | A1 * | 5/2008 | Atalar et al. .................. 607/116 |
| 2008/0132909 | A1 | 6/2008 | Jascob et al. |
| 2008/0171934 | A1 | 7/2008 | Greenan et al. |
| 2008/0171937 | A1 | 7/2008 | Dukesherer et al. |
| 2008/0172069 | A1 | 7/2008 | Dukesherer et al. |
| 2008/0228195 | A1 | 9/2008 | von Jako et al. |
| 2009/0088728 | A1 | 4/2009 | Dollar et al. |
| 2009/0118742 | A1 | 5/2009 | Hartmann et al. |
| 2009/0171187 | A1 | 7/2009 | Gerhart et al. |
| 2009/0204023 | A1 | 8/2009 | Goldenberg |
| 2009/0209947 | A1 | 8/2009 | Gordin et al. |
| 2010/0063383 | A1 | 3/2010 | Anderson et al. |
| 2010/0081965 | A1 | 4/2010 | Mugan et al. |
| 2010/0130852 | A1 | 5/2010 | Neidert et al. |
| 2010/0185083 | A1 | 7/2010 | Neidert et al. |

(56) References Cited

U.S. PATENT DOCUMENTS

| | | | |
|---|---|---|---|
| 2010/0210939 A1 | 8/2010 | Hartmann et al. | |
| 2010/0228117 A1 | 9/2010 | Hartmann | |
| 2010/0234724 A1 | 9/2010 | Jacobsen et al. | |
| 2010/0253361 A1* | 10/2010 | Nakamura et al. | 324/464 |
| 2010/0280363 A1 | 11/2010 | Skarda et al. | |
| 2010/0331763 A1 | 12/2010 | Wilson et al. | |
| 2011/0014705 A1 | 1/2011 | Leach et al. | |
| 2011/0060214 A1 | 3/2011 | Makower | |
| 2011/0066029 A1 | 3/2011 | Lyu et al. | |
| 2011/0118592 A1 | 5/2011 | Sobe et al. | |
| 2011/0251519 A1 | 10/2011 | Romoscanu | |
| 2011/0258842 A1 | 10/2011 | Dukesherer et al. | |
| 2011/0270081 A1 | 11/2011 | Burg et al. | |
| 2012/0172696 A1* | 7/2012 | Källbäck et al. | 600/373 |
| 2012/0197108 A1 | 8/2012 | Hartmann et al. | |
| 2012/0197109 A1 | 8/2012 | Hartmann et al. | |
| 2012/0197110 A1 | 8/2012 | Hartmann et al. | |
| 2012/0245665 A1 | 9/2012 | Friedman et al. | |
| 2012/0283570 A1 | 11/2012 | Tegg | |
| 2013/0066194 A1* | 3/2013 | Seter et al. | 600/424 |
| 2013/0137954 A1 | 5/2013 | Jacobsen et al. | |
| 2013/0317355 A1 | 11/2013 | JACOBSEN et al. | |
| 2014/0012130 A1* | 1/2014 | Jacobsen et al. | 600/424 |
| 2014/0148692 A1 | 5/2014 | Hartmann et al. | |
| 2014/0158555 A1* | 6/2014 | Nakamura et al. | 205/789 |
| 2014/0276004 A1 | 9/2014 | Strupeck et al. | |
| 2015/0005625 A1 | 1/2015 | Sobe et al. | |

FOREIGN PATENT DOCUMENTS

| | | |
|---|---|---|
| DE | 102009030731 A1 | 12/2010 |
| EP | 0425319 A2 | 5/1991 |
| EP | 1302172 A1 | 4/2003 |
| EP | 1552795 A1 | 7/2005 |
| EP | 1658818 A1 | 5/2006 |
| EP | 1743591 A2 | 1/2007 |
| EP | 1806756 A2 | 7/2007 |
| EP | 2123220 A1 | 11/2009 |
| EP | 2563260 A2 | 3/2013 |
| JP | 03-207344 B2 | 9/2001 |
| JP | 2007-527296 A | 9/2007 |
| JP | 2008194475 A | 8/2008 |
| JP | 2010082446 A | 4/2010 |
| WO | WO-9632060 A1 | 10/1996 |
| WO | WO-9729682 A1 | 8/1997 |
| WO | WO-9729684 A1 | 8/1997 |
| WO | WO-9940856 A1 | 8/1999 |
| WO | WO-0038571 A1 | 7/2000 |
| WO | WO-0134050 A2 | 5/2001 |
| WO | WO-2006096685 A1 | 9/2006 |
| WO | WO-2006116597 A2 | 11/2006 |
| WO | WO-2008105874 A1 | 9/2008 |
| WO | WO-2009152486 A1 | 12/2009 |
| WO | WO-2010049834 A1 | 5/2010 |
| WO | WO-2010124285 A1 | 10/2010 |
| WO | WO-2010144419 A2 | 12/2010 |
| WO | WO-2011137301 A2 | 11/2011 |
| WO | WO-2012103304 A1 | 8/2012 |
| WO | WO-2012103407 A1 | 8/2012 |
| WO | WO-2012103410 A1 | 8/2012 |
| WO | WO-2013062869 A1 | 5/2013 |

OTHER PUBLICATIONS

"InstaTrakTM 3500 plus—Cranial. Multi-application electromagnetic surgical navigation system for ENT, Cranial, and Spine procedures." GE Healthcare http://www.gehealthcare.com/euen/surgery/products/instatrak-3500-plus-cranial/index.html (printed Dec. 14, 2009).

"InstaTrakTm 3500 plus—Ent. Multi-application electromagnetic surgical navigation system for ENT and Cranial." GE Healthcare http://www.gehealthcare.com/euen/surgery/products/instatrak-3500-plus-ent/index.html (printed Dec. 14, 2009).

"InstaTrak® Image Guided Sinus Surgery, Introduction to the InstaTrak System." Sinus-Clear.com http://www.sinus-clear.com/instatrak.htm (printed Dec. 14, 2009).

"Mayfield® Skull Clamps and Headrest Systems," Mayfield® Surgical Devices Product Index, pp. 1-6, Dec. 2004 Integra LifeSciences Corporation.

"Medtronic O-Arm Multi-Dimensional Surgical Imaging System"; Brochure, 24pp, 2009.

"StealthStation_S7_Systeme Information Center in the OR," (2009) Medtronic, Inc.

"StealthStation® TRIA™ plus Treatment Guidance System," brochure, Medtronic Surgical Navigation Technologies (2004) 2 pages.

"The doctor can see you now" brochure. GE Medical Systems (2003) General Electric Company.

"TREON, StealthStation," brochure, Medtronic Surgical Navigation Technologies (2001) 8 pages.

Acclarent™ "Instructions for Use. Balloon Sinuplasty™ System. Relieva™ Devices, ReliENT™ Navigation System, and OptiLINK™ Extension." (Aug. 21, 2009) pp. 1-13.

Acclarent™ "Instructions for Use. Relieva Flex™ Sinus Guide Catheter, Relieva® Sinus Guide Catheter." (Sep. 19, 2009) pp. 1-6.

International Preliminary Report on Patentability mailed Nov. 15, 2012 for PCT/US2011/34475 claiming benefit of U.S. Appl. No. 13/097,243, filed Apr. 29, 2011.

International Search Report and Written Opinion mailed Feb. 6, 2013 for PCT/US2012/061086 claiming benefit of U.S. Appl. No. 13/281,001, filed Oct. 25, 2011.

International Search Report and Written Opinion mailed Jul. 6, 2012 for PCT/US2012/022840 claiming benefit to U.S. Appl. No. 13/016,762, filed Jan. 28, 2011.

International Search Report and Written Opinion mailed May 9, 2012 for PCT/US2012/022676 claiming benefit of U.S. Appl. No. 13/016,740, filed Jan. 28, 2011.

International Search Report and Written Opinion mailed May 9, 2012 for PCT/US2012/022846 claiming benefit of U.S. Appl. No. 13/016,765, filed Jan. 28, 2011.

International Search Report and Written Opinion mailed Oct. 31, 2011, claiming benefit of U.S. Appl. No. 13/097,243, filed Apr. 29, 2011.

Invitation to Pay Additional Fees mailed Dec. 17, 2012 for PCT/US2012/061086 claiming benefit of U.S. Appl. No. 13/281,001, filed Oct. 25, 2011.

Invitation to Pay Additional Fees mailed Jul. 25, 2011, claiming benefit of U.S. Appl. No. 13/097,243, filed Apr. 29, 2011.

Invitation to Pay Additional Fees mailed May 8, 2012 for PCT/US2012/022840 claiming benefit of U.S. Appl. No. 13/016,762, filed Jan. 28, 2011.

Medtronic Navigation, "StealthStation® AXIEM™ Electromagnetic Navigation . . . ", 2005, www.stealthstation.com/physician/spine/library/axiem_ent.jsp, printed Aug. 19, 2006 (2 pages).

Examiner's Report dated Dec. 18, 2013 for Canadian Application No. 2,797,359 claiming benefit of U.S. Appl. No. 13/097,243, filed Apr. 29, 2011.

Japanese Office Action dated Jan. 7, 2014 for Japan Application No. 2013-508273 claiming benefit of U.S. Application No. 13/097,243 filed Apr. 29, 2011.

"Flexible electronics," Dec. 19, 2012, XP055112518, en.wikipedia.org. Retrieved form the Internet: <URL:http://en.wikipedia.org/w/index.php?title=Flexible_electronics&oldid=528841651>[retrieved on Apr. 7, 2014]. (6 sheets).

"Flexible Printed Circuit Manufacturer—Capabilities," Aug. 16, 2012, XP055112534, fpcexpress.com. Retrieved from the Internet: URL: <http://web.archive.org/web/20120816030431/http://fpcexpress.com/capabilities.html>. [retrieved on Apr. 7, 2014][retrieved on May 8, 2014]. (3 sheets).

"Minco Bulletin FC-3," Jul. 31, 2002. XP055115671, Retrieved from the Internet: <URL:http://www.temflexcontrols.com/pdf/fc3.pdf> [retrieved on Apr. 29, 2014]. (1 sheet).

"Sectional design standard for flexible printed boards," Internet Citation, Nov. 30, 1998, pp. 1-35, XP002691487, Retrieved form the Interent: <URL:http://222.184.16.210/smt/tzxt/bz/IPC-2223.pdf>. [retrieved on Feb. 1, 2013].

(56) References Cited

OTHER PUBLICATIONS

International Preliminary Report on Patentability and Written Opinion mailed May 8, 2014 for PCT/US2012/061086 claiming benefit of U.S. Appl. No. 13/281,001, filed Oct. 25, 2011.
International Search Report and Written Opinion mailed Apr. 23, 2014 for PCT/US2014/012786 claiming benefit of U.S. Appl. No. 13/748,150, filed Jan. 23, 2013.
International Search Report and Written Opinion mailed May 12, 2014 for PCT/US2014/012967 claiming benefit of U.S. Appl. No. 13/751,032, filed Jan. 25, 2013.
http://oxforddictionaries.com/definition/english/barrel (accessed Dec. 3, 2012).
International Preliminary Report on Patentability mailed Aug. 8, 2013 for PCT/US2012/022676 claiming benefit of U.S. Appl. No. 13/016,740, filed Jan. 28, 2011.
International Preliminary Report on Patentability mailed Aug. 8, 2013 for PCT/US2012/022840 claiming benefit of U.S. Appl. No. 13/016,762, filed Jan. 28, 2011.
International Preliminary Report on Patentability mailed Aug. 8, 2013 for PCT/US2012/022846 claiming benefit of U.S. Appl. No. 13/016,765, filed Jan. 28, 2011.
Chinese Office Action dated Sep. 3, 2014 for Chinese Application No. 201180031075.0 claiming benefit of PCT/US2011/034475 filed Apr. 29, 2011, claiming benefit from U.S. Appl. No. 61/330,024, filed Apr. 30, 2010 and U.S. Appl No. 13/097,243, filed Apr. 29, 2011.
International Preliminary Report on Patentability and Written Opinion mailed Sep. 22, 2011 for PCT/US2010/026655 claiming benefit of U.S. Appl. No. 12/400,451 filed Mar. 10, 2009.
International Search Report and Written Opinion mailed Oct. 27, 2014 for PCT/US2014/028100 claiming benefit of U.S. Application No. 14/209,696 filed Mar. 13, 2014.
International Search Report mailed Jul. 15, 2010 for PCT/US2010/026655 claiming benefit of U.S. Appl. No. 12/400,451 filed Mar. 10, 2009.
Invitation to Pay Additional Fees and Where Applicable, Protest Fee mailed Aug. 14, 2014 for PCT/US2014/028100 claiming benefit of U.S. Appl. No. 14/209,696, filed Mar. 13, 2014.
Chinese Office Action dated Apr. 3, 2015 for Chinese Application No. 201180031075.0 claiming benefit of PCT/US2011/034475 filed Apr. 29, 2011, claiming benefit from U.S. Appl. No. 61/330,024, filed Apr. 30, 2010 and U.S. Appl. No. 13/097,243, filed Apr. 29, 2011.
Communication pursuant to Article 94(3) Epc for European Application No. 12703208.4 -1654 dated Apr. 24, 2015.
International Preliminary Report on Patentability and Written Opinion mailed on Aug. 6, 2015 for PCT/US2014/012786 claiming benefit of U.S. Appl. No. 13/748,150, filed Jan. 23, 2013.
International Preliminary Report on Patentability and Written Opinion mailed on Aug. 6, 2015 for PCT/US2014/012967 claiming benefit of U.S. Appl. No. 13/751,032, filed Jan. 25, 2013.
International Preliminary Report on Patentability and Written Opinion mailed Sep. 24, 2015 for PCT/US2014/028100 claiming benefit to U.S. Appl. No. 14/209,696, filed Mar. 13, 2014.
International Preliminary Report on Patentability mailed Oct. 27, 2015 for PCT/US2014/034022 claiming benefit of U.S. Appl. No. 13/871,616, filed Apr. 26, 2013.

* cited by examiner

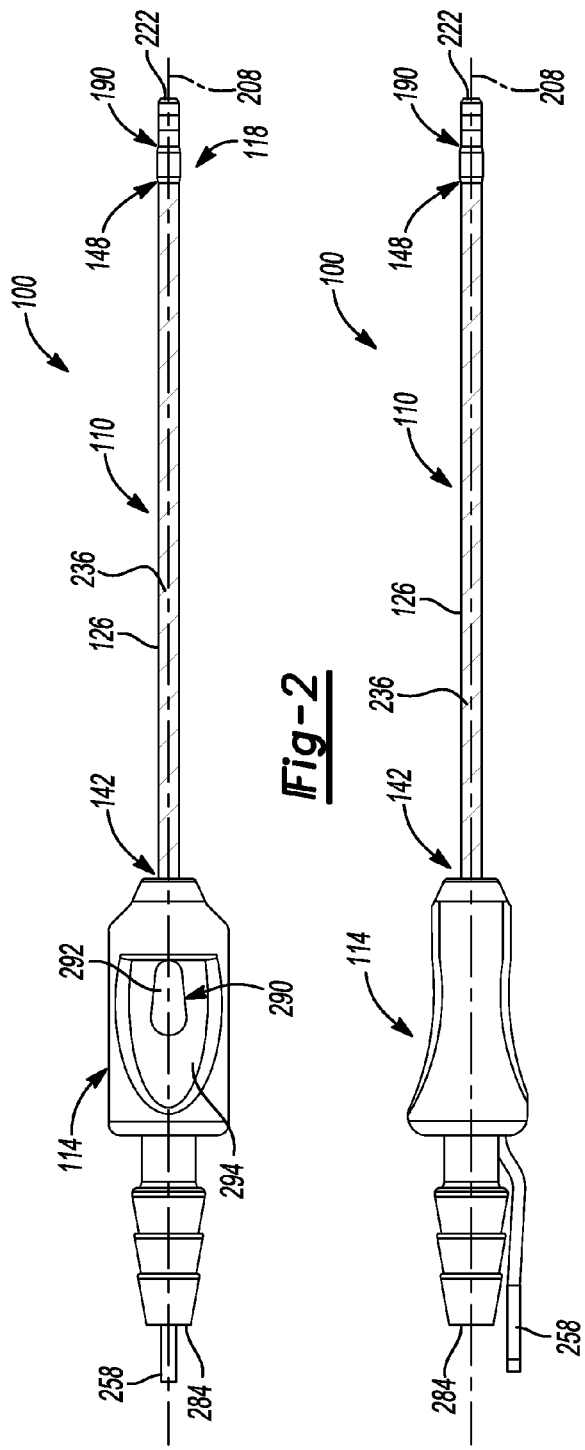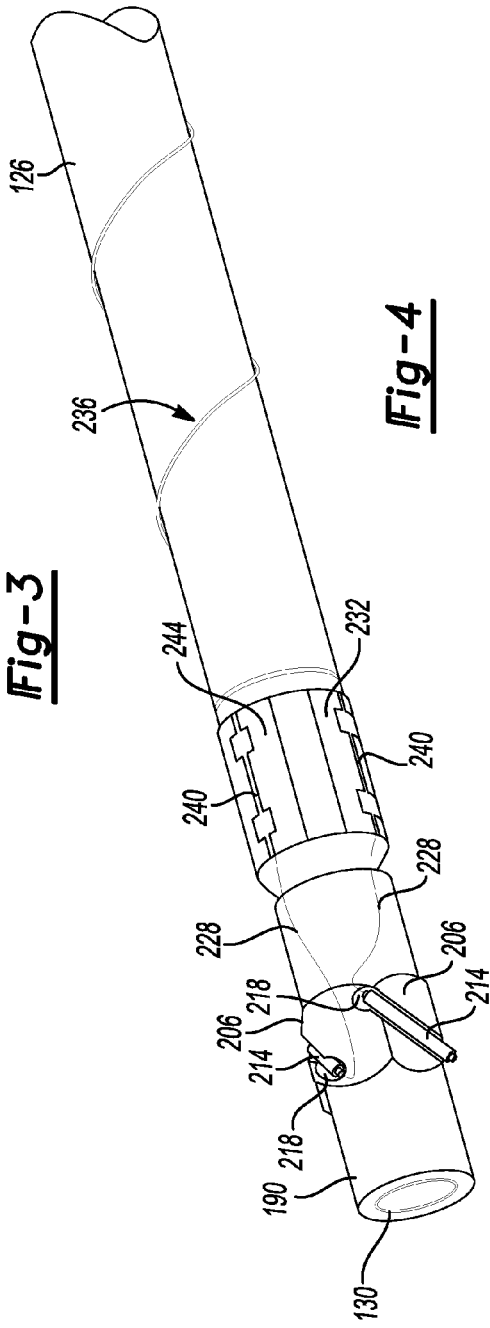

FLEXIBLE CIRCUIT ASSEMBLIES

CROSS-REFERENCE TO RELATED APPLICATIONS

This application is a continuation-in-part of U.S. application Ser. No. 13/097,243 filed on Apr. 29, 2011, which claims the benefit of U.S. Provisional Patent Application No. 61/330,024 filed on Apr. 30, 2010. This application is also a continuation-in-part of U.S. application Ser. No. 12/400,951 filed on Mar. 10, 2009. The disclosures of the above applications are incorporated herein by reference.

FIELD

The present disclosure relates generally to a flexible circuit sheet and, more particularly, a flexible circuit sheet for a surgical instrument.

BACKGROUND

The statements in this section merely provide background information related to the present disclosure and may not constitute prior art.

Surgical procedures can be performed on anatomies such as the human anatomy for providing a therapy to the anatomy. One area of surgery includes procedures performed on facial cavities of a patient such as on the ear, nose or throat (ENT). In such a procedure, a surgical instrument such as a suction device may be inserted into such a cavity to perform a procedure for example. Because the viewing angle of a surgeon at the area of interest can be obscured by the surrounding tissue of the cavity, the ability of a surgeon to effectively apply a therapy, such as a suction procedure, can be reduced. In some procedures, it may also be difficult to effectively guide the surgical instrument through various shaped cavities of the anatomy. In an effort to address this difficulty, instruments have been developed that include flexible elongated portions configured to be permanently flexible. While these flexible instruments can conform to internal cavities of the anatomy, they do not retain any specific configuration, such that they are generally not suitable for certain procedures, such as an ENT suction procedure.

In navigation systems, instruments are provided with tracking devices. Sometimes, however, such tracking devices can be difficult to manipulate or cumbersome to couple to the instrument, especially instruments with the flexible elongated portions. For example, it can be difficult to electrically couple the tracking devices to associated lead wires relative to the flexible elongated portion. In other instances, the tracking devices can be positioned in a handle or proximal region of the instrument such that if the distal tip moves or is moved relative to the handle, the distal tip can no longer be accurately tracked.

SUMMARY

This section provides a general summary of the disclosure, and is not a comprehensive disclosure of its full scope or all of its features.

In one form, a flexible circuit assembly for a medical device is provided in accordance with the teachings of the present disclosure. The flexible circuit assembly can include a base layer, a plurality of circuit traces and an insulative layer. The plurality of circuit traces can each be coupled to a pair of circuit pads, and the circuit traces can be formed on an upper side of the base layer. The insulative layer can be formed over the circuit traces to isolate the circuit traces from an external environment. The base layer, plurality of circuit traces and insulative layer can form a flexible circuit sheet. The base layer and the insulative layer can include material properties and a thickness configured to facilitate the flexible circuit sheet being flexible such that the flexible circuit sheet is adapted to conform to a non-planar surface of the medical device.

In another form, a flexible circuit assembly for a medical device is provided in accordance with the teachings of the present disclosure. The flexible circuit assembly can include a base layer, a plurality of circuit traces, and an insulative layer. The plurality of circuit traces can each be coupled to first and second circuit pads, and the plurality of circuit traces can be formed on an upper side of the base layer. The insulative layer can be formed over the circuit traces so as to isolate the circuit traces from an external environment. The base layer, plurality of circuit traces and insulative layer can form a flexible circuit sheet. The base layer and the insulative layer can include material properties combined with an overall thickness of the flexible circuit sheet of less than or equal to 0.05 mm that facilitate the flexible circuit sheet being flexible such that the flexible circuit sheet is adapted to conform to a non-planar surface of the medical device.

In yet another form, a flexible circuit assembly for a medical device is provided in accordance with the teachings of the present disclosure. The flexible circuit assembly can include a base layer, a plurality of circuit traces and an insulative layer. The plurality of circuit traces can each be coupled to first and second circuit pads, and the plurality of circuit traces can be formed on an upper side of the base layer. The insulative layer can be formed over the circuit traces so as to isolate the circuit traces from an external environment. The base layer, plurality of circuit traces and insulative layer can form a flexible circuit sheet configured to be coupled to a non-planar surface of a flexible component of the medical device. The base layer and the insulative layer can include material properties combined with an overall thickness of the flexible circuit sheet of between approximately 0.04 mm and 0.05 mm and a corresponding bend radius of between approximately 0.4 mm and 0.5 mm that facilitate the flexible circuit sheet being flexible such that the flexible circuit sheet is configured to conform to the non-planar surface and bend or flex with bending of the flexible component.

Further areas of applicability will become apparent from the description provided herein. It should be understood that the description and specific examples are intended for purposes of illustration only and are not intended to limit the scope of the present teachings.

DRAWINGS

The present teachings will become more fully understood from the detailed description, the appended claims and the following drawings. The drawings are for illustrative purposes only of selected embodiments and not all possible limitations, and are not intended to limit the scope of the present disclosure.

FIG. 2 is a top plan view of an exemplary malleable suction instrument for use with the navigation system according to the principles of the present disclosure;

FIG. 3 is a side view of the exemplary suction instrument according to the principles of the present disclosure;

FIG. 4 is a partial perspective view of a distal region of the exemplary suction instrument having an exemplary flexible circuit sheet according to the principles of the present disclosure;

DESCRIPTION OF THE VARIOUS EMBODIMENTS

Figure 1:
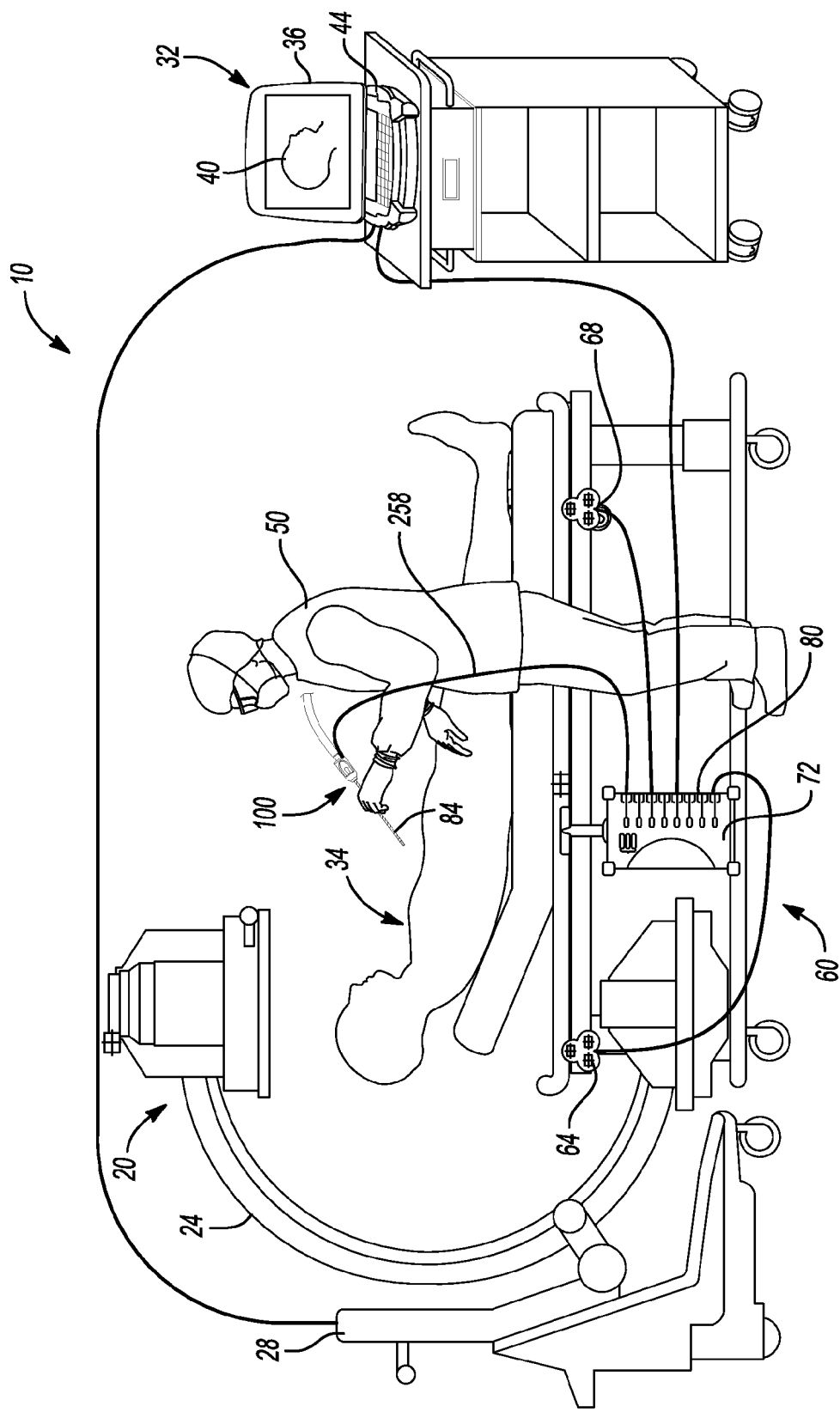
FIG. 1 is a perspective view of an exemplary navigation system according to the principles of the present disclosure.

The following description is merely exemplary in nature and is not intended to limit the present disclosure, its application, or uses. It should be understood that throughout the drawings, corresponding reference numerals indicate like or corresponding parts and features with the various elements in each view being drawn to scale. Although the following description is related generally to a flexible circuit sheet operatively associated with an exemplary flexible or malleable suction instrument, it will be appreciated that the flexible circuit sheet can be associated with various devices and/or instruments, including various other surgical instruments.

Various exemplary embodiments are provided so that this disclosure will be thorough, and will fully convey the scope to those who are skilled in the art. Numerous specific details are set forth such as examples of specific components, devices, systems and/or methods, to provide a thorough understanding of exemplary embodiments of the present disclosure. It will be apparent to those skilled in the art that specific details need not be employed, that exemplary embodiments may be embodied in many different forms and that neither should be construed to limit the scope of the disclosure. In some exemplary embodiments, well-known processes, well-known device structures, and well-known technologies are not described in detail.

FIG. 1 is a diagram schematically illustrating an overview of an image-guided navigation system 10 for use in the non-line-of-site navigating of a surgical instrument 100, such as a navigable malleable suction device or suction instrument, according to various exemplary embodiments of the present disclosure. Exemplary navigation systems include those disclosed in U.S. Pat. No. 7,366,562, issued on Apr. 29, 2008 to John H. Dukesherer et al. and U.S. Pat. App. Pub No. 2008/0132909, published Jun. 5, 2008, to Bradley A. Jascob et al., both incorporated herein by reference. Commercial navigation systems include the StealthStation® AxiEM™ Surgical Navigation System sold by Medtronic Navigation, Inc. having a place of business in Louisville, Colo., USA. It should be appreciated that while the navigation system 10 and suction instrument 100 are generally described in connection with an ear, nose and throat (ENT) procedure, navigation system 10 and suction instrument 100 can be used in various other appropriate procedures.

Generally, the navigation system 10 can be used to track a location of an exemplary suction instrument 100, including a distal tip or end thereof, that includes an exemplary flexible printed circuit sheet 232 associated therewith, as will be described herein. Navigation system 10 can generally include an optional imaging system 20, such as a fluoroscopic X-ray imaging device configured as a C-arm 24 and an image device controller 28. The C-arm imaging system 20 can be any appropriate imaging system, such as a digital or CCD camera, which are well understood in the art. Image data obtained can be stored in the C-arm controller 28 and sent to a navigation computer and/or processor controller or work station 32 having a display device 36 to display image data 40 and a user interface 44. The work station 32 can also include or be connected to an image processor, navigation processor, and a memory to hold instruction and data. The work station 32 can include an optimization processor that assists in a navigated procedure. It will also be understood that the image data is not necessarily first retained in the controller 28, but may also be directly transmitted to the workstation 32. Moreover, processing for the navigation system and optimization can all be done with a single or multiple processors all of which may or may not be included in the work station 32.

The work station 32 provides facilities for displaying the image data 40 as an image on the display device 36, saving, digitally manipulating, or printing a hard copy image of the received image data. The user interface 44, which may be a keyboard, mouse, touch pen, touch screen or other suitable device, allows a physician or user 50 to provide inputs to control the imaging device 20, via the C-arm controller 28, or adjust the display settings of the display device 36.

With continuing reference to FIG. 1, the navigation system 10 can further include a tracking system, such as an electromagnetic (EM) tracking system 60. The discussion of the EM tracking system 60 can be understood to relate to any appropriate tracking system. The EM tracking system 60 can include a localizer, such as a coil array 64 and/or second coil array 68, a coil array controller 72, a navigation probe interface 80, and the trackable suction instrument 100. Instrument 100 can include an instrument tracking device or devices 84, as will be discussed herein. Briefly, the tracking device 84 can include an electromagnetic coil to sense a field produced by the localizing coil arrays 64, 68 and provide information to the navigation system 10 to determine a location of the tracking device 84. The navigation system 10 can then determine a position of a distal tip of the suction instrument 100 to allow for navigation relative to the patient 34 and patient space.

The EM tracking system 60 can use the coil arrays 64, 68 to create an electromagnetic field used for navigation. The coil arrays 64, 68 can include a plurality of coils that are each operable to generate distinct electromagnetic fields into the navigation region of the patient 34, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The coil arrays 64, 68 can be controlled or driven by the coil array controller 72. The coil array controller 72 can drive each coil in the coil arrays 64, 68 in a time division multiplex or a frequency division multiplex manner. In this regard, each coil may be driven separately at a distinct time or all of the coils may be driven simultaneously with each being driven by a different frequency.

Upon driving the coils in the coil arrays 64, 68 with the coil array controller 72, electromagnetic fields are generated within the patient 34 in the area where the medical procedure is being performed, which is again sometimes referred to as patient space. The electromagnetic fields generated in the patient space induce currents in the tracking device 84 positioned on or in the suction instrument 100. These induced signals from the tracking device 84 can be delivered to the navigation probe interface 80 and subsequently forwarded to the coil array controller 72. The navigation probe interface 80 can also include amplifiers, filters and buffers to directly interface with the tracking device 84 in the instrument 100. Alternatively, the tracking device 84, or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled directly to the navigation probe interface 80.

The tracking system 60, if it is using an electromagnetic tracking assembly, essentially works by positioning the coil arrays 64, 68 adjacent to the patient 32 to generate a magnetic field, which can be low energy, and generally referred to as a navigation field. Because every point in the navigation field or patient space is associated with a unique field strength, the electromagnetic tracking system 60 can determine the position of the instrument 100 by measuring the field strength at the tracking device 84 location. The coil array controller 72 can receive the induced signals from the tracking device 84 and transmit information regarding a location, where location information can include both x, y, and z position and roll, pitch, and yaw orientation information, of the tracking device 84 associated with the tracked suction instrument 100. Accordingly, six degree of freedom (6 DOF) information can be determined with the navigation system 10.

Referring now to FIGS. 2-10, the navigated malleable surgical instrument 100 will be described in greater detail. In one exemplary configuration, the malleable surgical instrument 100 can be used for suction, including fluid and tissue removal in ENT procedures. It should be appreciated, however, that the navigated malleable surgical instrument 100 can be used in various other surgical procedures as may be desired and can be provided in the form of a malleable or flexible endoscope, a malleable or flexible catheter, and/or a malleable cannula. Thus, while the following description continues with reference to a navigated malleable suction instrument 100, the discussion is also applicable to the surgical instruments discussed above.

Figure 6:
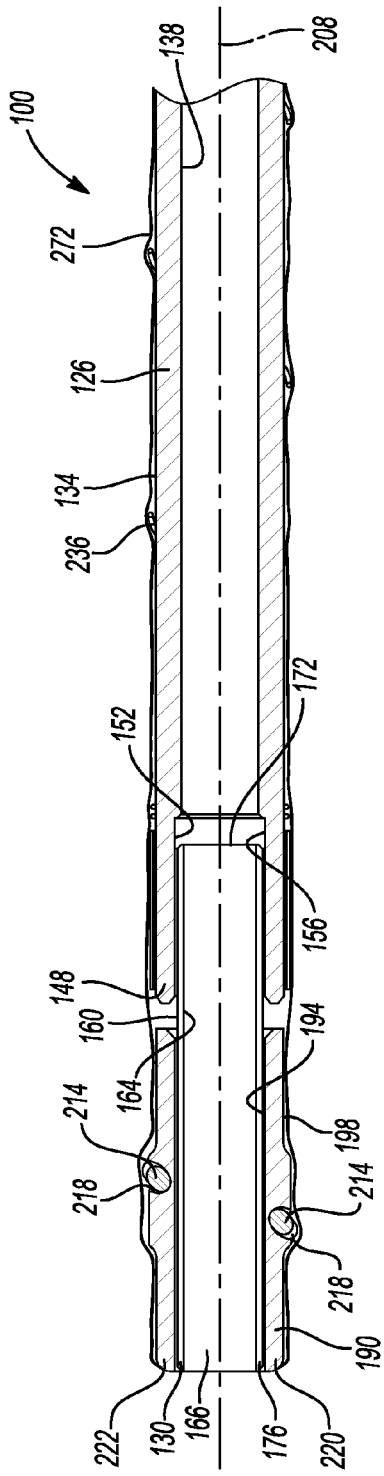
FIG. 6 is a partial sectional view of the exemplary suction instrument of FIG. 5 according to the principles of the present disclosure.

Suction instrument 100 can include a tube assembly 110, a handle assembly 114 and a tracking sensor arrangement 118. Suction instrument 100 can be configured for a single use such that it would be disposed after such use. The tube assembly 110 can include a malleable elongated tubular body 126 and an insert portion 130. The tubular body 126 can include an outer diameter 134 and an inner diameter 138 and can have a first end 142 coupled to the handle assembly 114 and a second opposite end 148 configured to receive insert portion 130, as shown in FIG. 6. The second end 148 can include an internal annular recess 152 having an inner diameter 156 greater than the inner diameter 138 of the remaining portion of body 126, as also shown in FIG. 6. The malleable elongated body 126 can be formed from various aluminum alloys, such as AL 3003-O, various stainless steel alloys, such as 304 annealed, as well as various other materials including titanium, niobium, molybdenum, tantalum, nitinol, vinyl, and multi-lumen materials, such that it is malleable to facilitate being bent or formed into various configurations and retaining the bent or formed configuration, as will be discussed herein. The body 126 can also be provided in various lengths and diameters, including 7, 9 and 12 French diameters.

The insert portion 130 can be configured to provide non-malleable support for at least the tracking sensor 84. Insert portion 130 can include an outer diameter 160 substantially equal to the inner diameter 156 of annular recess 152, and an inner diameter 164 substantially equal to the inner diameter 138 of malleable elongated body 126, as also shown in FIG. 6. In this manner, the substantially equal inner diameters 138, 164 can provide for a substantially constant flow path 166 for suction. It should be appreciated, however, that the inner diameters 138, 164 can also be provided with varying dimensions. The insert portion 130 can also include an exemplary axial length of 10 to 15 mm, including 14 mm. Insert portion 130 can include a first end 172 and a second opposite end 176. The first end 172 of the insert portion 130 can be received in annular recess 152, as shown in FIG. 6. Insert portion can include a rigid construction to facilitate receiving and housing tracking device 84, as will be described herein. In this manner, insert portion 130 can be formed or manufactured from stainless steel or other biocompatible rigid materials such that insert portion 130 is not malleable like elongated body 126. The insert portion can also include an exemplary axial length of approximately 10 mm.

Figure 5:
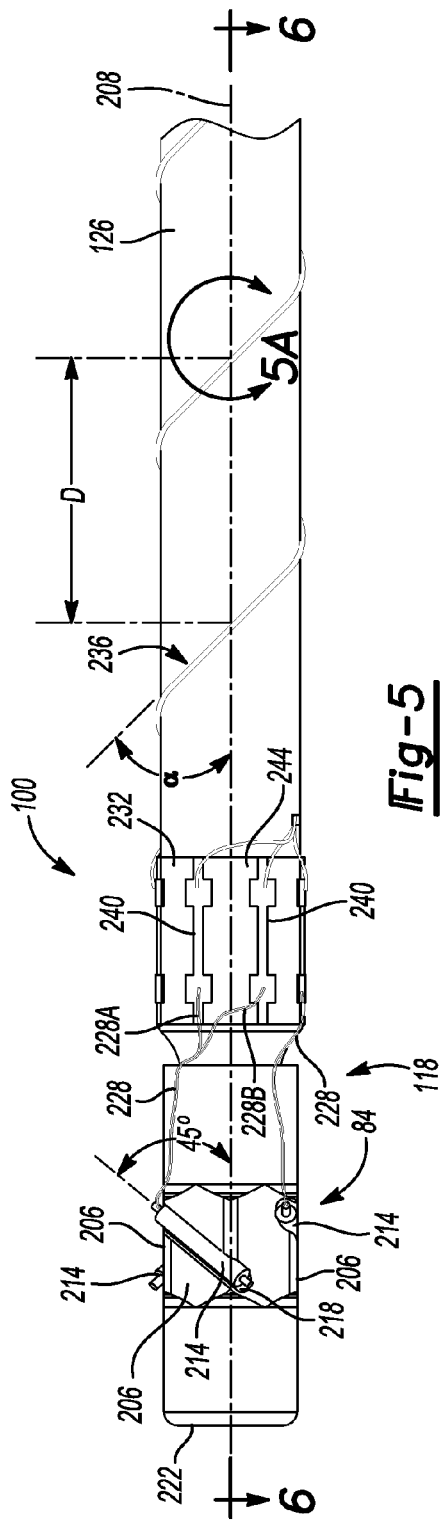
FIG. 5 is a partial side view of the distal region of the exemplary suction instrument associated with the exemplary flexible circuit sheet according to the principles of the present disclosure.

Insert portion 130 can include a sleeve 190 received on an exterior thereof, as shown in FIGS. 5 and 6. Sleeve 190 can include an inner diameter 194 substantially equal to the outer diameter of insert portion 130, and an outer diameter 198 substantially equal to the outer diameter 134 of body 126. It should be appreciated that sleeve 190 can also be configured with different diameters relative to body 126. Sleeve 190 can extend over a portion of insert 130 from the first end 172 of the insert portion 130 towards the second end, as shown in FIG. 6. In one exemplary configuration, sleeve 190 can extend from the first end 172 and contact the first end 142 of body 126 when the insert portion 130 is coupled to annular recess 152 of body 126. In another exemplary configuration, sleeve 190 can extend from the first end 172 of body portion 130 in a similar manner as discussed above, but can stop short of the first end 142 of body 126, as shown in FIG. 6. Sleeve 190 can be fixed to insert portion 130, and insert portion 130 can be fixed to annular recess 152 with an appropriate adhesive. Sleeve 190 can be formed of a polymeric material or other suitable materials. Sleeve 190 can also include a first end 220 configured to substantially align with the second end 176 of insert 130. The first end 220 can include a rounded or chamfered blunt distal tip or end part 222 such that it can be placed against surrounding tissue during a suction procedure without cutting or damaging such tissue. In one exemplary configuration, end part 222 can extend over insert portion 130 so as to prevent cutting or damaging tissue.

With particular reference to FIGS. 4 and 5, sleeve 190 can include a plurality of flattened sections 206 configured to facilitate receiving and supporting the tracking sensor arrangement 118, as will be described herein. In one exemplary configuration, sleeve 190 can include at least three flattened sections 206 configured to attachably receive tracking device 84. In this configuration, the tracking device 84 can include three coil assemblies 214, as will be described herein. Briefly, in one exemplary configuration, the three coil assemblies 214 can each include a cylindrical configuration as shown in FIGS. 4 and 5, having an overall axial length of approximately 1.5 mm to 2 mm, an overall diameter of approximately 0.3 to 0.5 mm, and a plurality of wire windings wound along a cylindrical base to form the cylindrical configuration. The plurality of windings can form the coil assembly 214 having the generally uniform cylindrical configuration, as generally shown in FIG. 5. Each flattened section 206 can include a slot or depression 218 formed therein and configured to receive a corresponding coil assembly 214, as shown for example in FIGS. 5 and 6. Each slot 218 can be formed in the corresponding flattened section 206 at a 35 to 75 degree angle, including a 55 degree angle, to a longitudinal axis 208 of the tube assembly 110. In one exemplary configuration, each slot 218 can be formed at a 55 degree angle to longitudinal axis 208, as shown in FIG. 5. Each of the three flattened sections 206 can be positioned equidistantly or 120 degrees around a circumference of sleeve 190 so that the three coil assemblies 214 are therefore likewise positioned equidistantly around the circumference of sleeve 90, as also generally shown in FIGS. 4-6. It should be appreciated that the coil assemblies can also be coupled to the sleeve without the flattened sections 206, and can be aligned at different orientations relative to the longitudinal axis, including parallel thereto. In this regard, the sleeve 190 can include an outer surface with a circular shape in cross-section configured to receive the coil assemblies 214.

The coil assemblies 214 can include three coil assemblies as described above that cooperate with the navigation system 10 such that 6 DOF tracking information can be determined. It should be appreciated, however, that two coil assemblies 214 could also be used in conjunction with navigation system 10 such that 6 DOF tracking information can also be determined. In a configuration where three coil assemblies 214 are utilized, two of the three coil assemblies can be positioned at an angle relative to the longitudinal axis 208 with the third coil assembly being positioned at an angle relative to the longitudinal axis 208 or parallel thereto. The three coil assemblies 214 can also each be positioned at an angle relative to each other. As discussed above, an exemplary angle of the three coil assemblies 214 relative to the longitudinal axis 208 can be 55 degrees, which also provides for optimal packaging and spacing of the coil assemblies circumferentially around sleeve 190. It should be appreciated that while an angle of 55 degrees has been discussed, other angles could be utilized with coil assemblies 214 and instrument 100 as may be required. It should also be appreciated, as discussed above, that the coil assemblies could be positioned parallel or perpendicular to the longitudinal axis 208.

In a configuration where tracking device 84 includes two coil assemblies 214, the two coil assemblies can similarly be positioned equidistant or 180 degrees spaced around an outer perimeter of sleeve 190, as well as can each be positioned at an angle relative to each other and at an angle relative to the longitudinal axis 208 of the tube assembly 110. In this configuration, the two coil assemblies can also cooperate with navigation system 10 such that 6 DOF tracking information can be determined. In one exemplary configuration, the two coil assemblies 214 can be positioned at an angle of about 35 to 75 degrees, including about 55 degrees relative to longitudinal axis 208 of the tube assembly 210.

Figure 8:
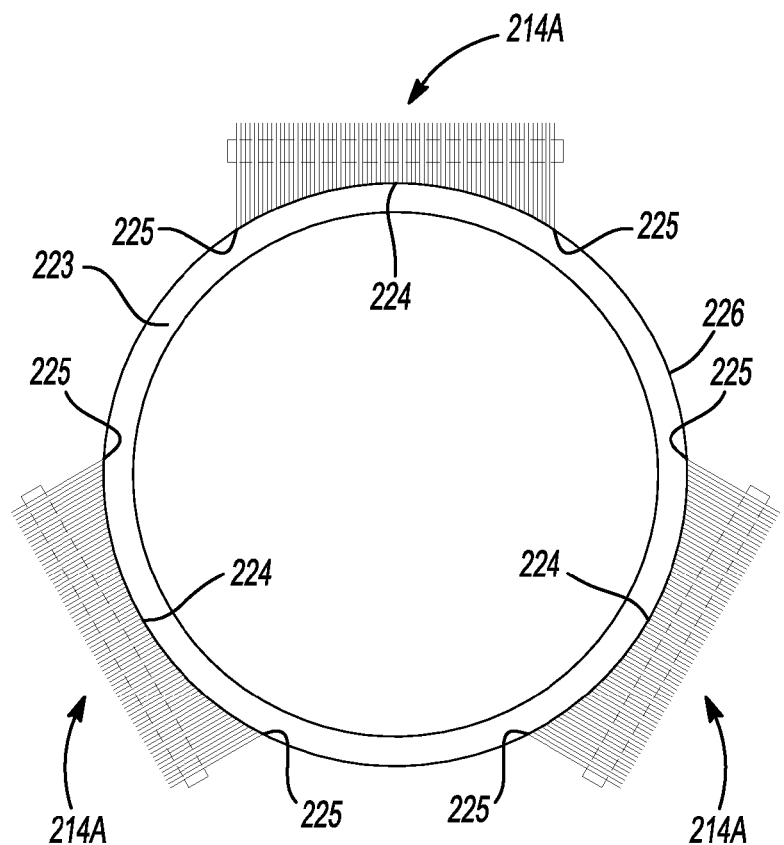
FIGS. 8 and 9 illustrate views of exemplary alternative tracking sensor configurations according to the principles of the present disclosure.
Figure 9:
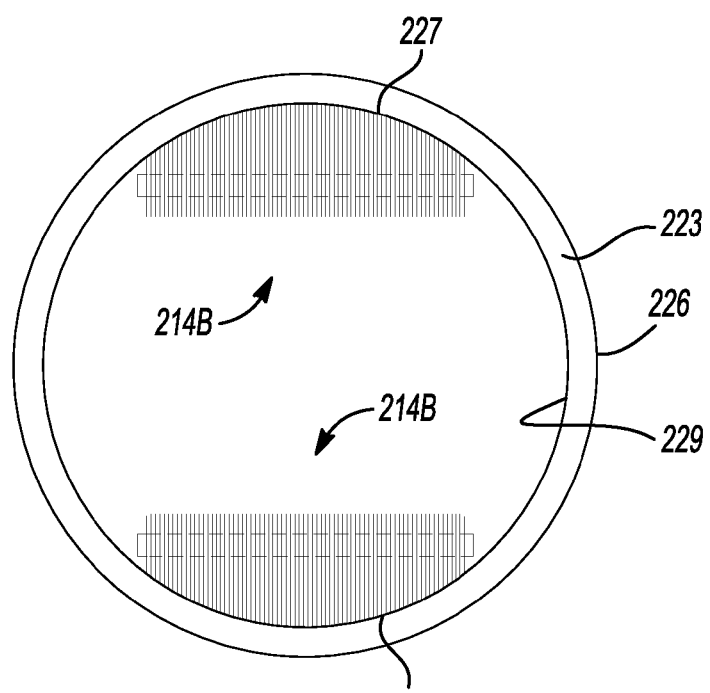

With additional reference to FIGS. 8 and 9, two exemplary coil assemblies 214A and 214B having alternative winding configurations are illustrated operatively associated with an exemplary tubular structure 223 of an exemplary instrument. Coil assemblies 214A and 214B can each include an overall non-linear shape as compared to the overall cylindrical configuration of coils assemblies 214 shown in FIG. 5. Coil assembly 214A can include a central arcuate depression or concavity 224 such that the depression 224 has a smaller outer diameter than opposed ends 225 of the plurality of windings, as generally shown in FIG. 8. The winding configuration of coil assembly 214A can provide an ability to maximize an amount of coil windings on a base wire while working towards minimizing an overall outer dimension or size of an instrument. In this regard, coil assembly 214A is shown in FIG. 8 with the arcuate depression 224 substantially conforming to an outer surface 226 of the tubular structure 223 such that the coil assembly or assemblies 214A essentially nest around the outer surface 226 of the tubular structure. In this regard, because of the general clearance provided by a cylindrical coil assembly positioned adjacent to an outer diameter of the tubular structure 223, a gap or space 221 on either end of the coil can include additional windings without effectively increasing the overall outer diameter of the entire assembly. This can allow for greater or stronger sensitivity in the navigated space.

With particular reference to FIG. 9, coil assembly 214B can include an overall arcuate convex shape 227 configured to conform to and nest within an inner diameter 229 of the exemplary tubular structure. Similar to coil assembly 214A, such a configuration can provide for maximizing an amount of windings on the base wire while also working towards minimizing the inner diameter 229 of the tubular structure 223 that would be required to receive one or more coil assemblies 214B.

Figure 5A:
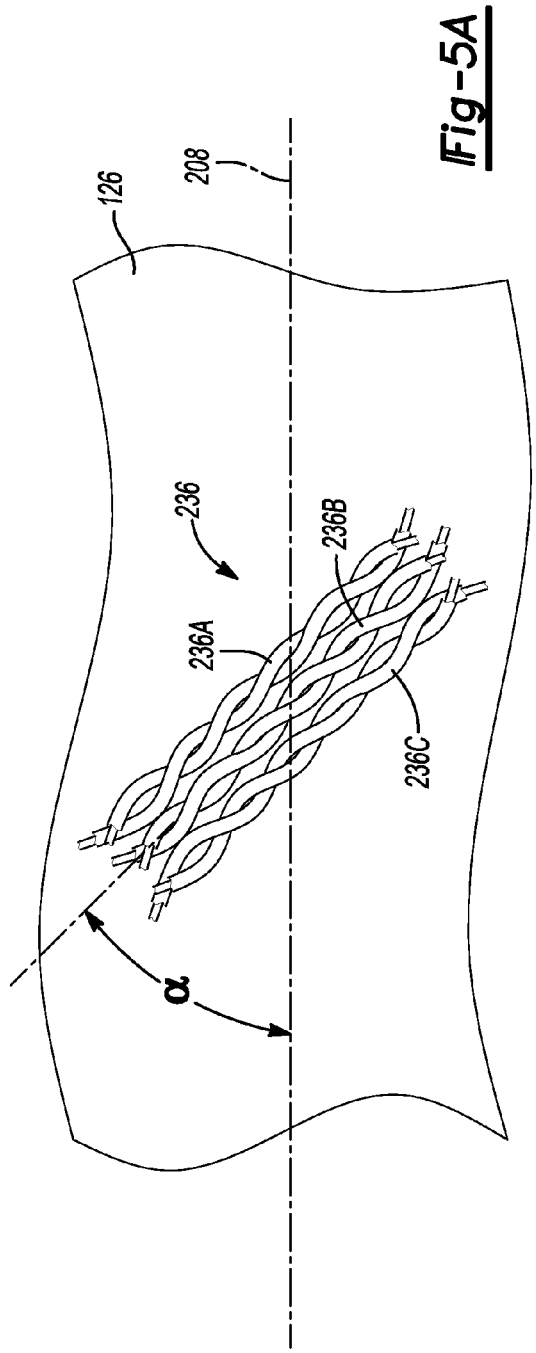
FIG. 5A is an exploded view of an exemplary wire routing configuration according to the principles of the present disclosure.

With particular reference to FIGS. 5 and 5A, the tracking sensor arrangement 118 will now be described in detail. Tracking sensor arrangement 118 can include the tracking device 84 having the two or three coil assemblies 214, as well as a first set of lead wires 228, the flexible printed circuit board or sheet 232 and a second set of lead wires 236. The first set of lead wires 228 can include a pair of lead wires 228A and 228B for each coil assembly 214, as generally shown in FIG. 5. Each respective pair of lead wires 228A and 228B can be routed to a first end of a respective pair of circuit connections 240 on flexible printed circuit sheet 232. As will be discussed in greater detail below, the flexible circuit sheet 232 can facilitate improving the time and cost associating with terminating fine wires utilized in medical and other instruments while also providing the flexibility necessitated for such instruments. It should be appreciated that while tracking device 84 is described as having three coil assemblies, more or less coil assemblies can be utilized as may be desired or required depending on, for example, characteristics of the navigation system being utilized as well as the number of degrees of freedom desired.

The flexible printed circuit sheet 232 can include a flexible backing or base layer 244 such that it can readily conform to the contour of an outer surface of the body 126, as shown for example in FIG. 4. The flexible printed circuit sheet 232 can wrap entirely or partially around a perimeter of the body 126 and can be positioned adjacent the second end 148 of body 126, as generally shown in FIGS. 5 and 6. In this manner, the insert portion 130, in its inserted position shown in FIG. 6, can be under all or substantially all of the flexible printed circuit sheet 232. The rigid insert portion 130 can thus prevent the malleable body 126 from bending or flexing in a region of the flexible printed circuit sheet 232. In one exemplary configuration, the flexible printed circuit sheet 232 can be an integral part of sleeve 190. In another exemplary configuration, flexible printed circuit sheet 232 can be positioned in a similar manner on sleeve 190. In this configuration, flexible printed circuit sheet 232 can be positioned on sleeve 190 between coil assemblies 214 and the end of sleeve 190 adjacent the second end 148 of body 126.

The second set of lead wires can include three respective pairs of wires 236A, 236B, 236C, as generally shown in FIG. 5 with reference to the partial exploded view in FIG. 5A. It should be appreciated that while FIGS. 2-5, 6-7 and 10 show the second set of lead wires 236 as one element, this is for illustration purposes only and it should be understood that the second set of lead wires shown in FIGS. 2-5, 6-7 and 10 include the three respective pairs of lead wires 236A-C, as shown in FIG. 5A. Each pair of lead wires 236A-C can be twisted together and positioned adjacent each other, as also shown in FIG. 5A. The twisted pairs 236A-C of wires can reduce electrical interference or cross-talk between each pair of adjacent lead wires. Each pair of lead wires can be connected to a single coil assembly 214 via the flexible printed circuit sheet 232. The lead wires can also include a Teflon coating or other appropriate lubricous or friction reducing coating on an outer surface thereof. Each pair of lead wires 236A-C can be coupled to an opposite end of respective circuit pads 240 on the flexible printed circuit sheet 232. It should be appreciated that the lead wires 228 could alternatively extend up the body 126 as a twisted pair of lead wires without the use of the flexible printed circuit sheet 232, or could extend up to and be terminated directly to the respective twisted pair of lead wires 236.

The second set of lead wires 236, which includes the three pairs of twisted wires 236A-C, can be helically wound around elongated body 126 from the flexible printed circuit sheet 232 to the second end 148, as generally shown for example in FIGS. 3-5A. The wires 236 can be wound around the outside of body 126 at an angle α relative to the longitudinal axis 208 of approximately 0 to 85 degrees, including about 30 degrees, as generally shown in FIGS. 5 and 5A. Each revolution of wires 236 around body 126 can be spaced apart from each other by a distance D of approximately 2 to 45 mm, including about 5 mm, as shown with reference to FIG. 5. In one exemplary configuration, the range can include from about 15-45 mm. The helical winding of the wires 236 at an acute angle relative to the longitudinal axis along with the relatively close spacing of the wires and the Teflon coating facilitate being able to bend the malleable body 126 at significant angles, including beyond ninety degrees, without breaking or otherwise damaging the wires 236, as will be discussed herein. It should be appreciated that the wires 236 can also be positioned along body 126 in a single revolution from the flexible printed circuit sheet 232 or the tracking device 84 to the second end 148. In this regard, the revolution spacing can be from about 2 mm to a length of the body 126. The wires 236 can also be positioned along body 126 from the flexible printed circuit sheet 232 to the second end 148 without being wound around body 136.

Figure 7:
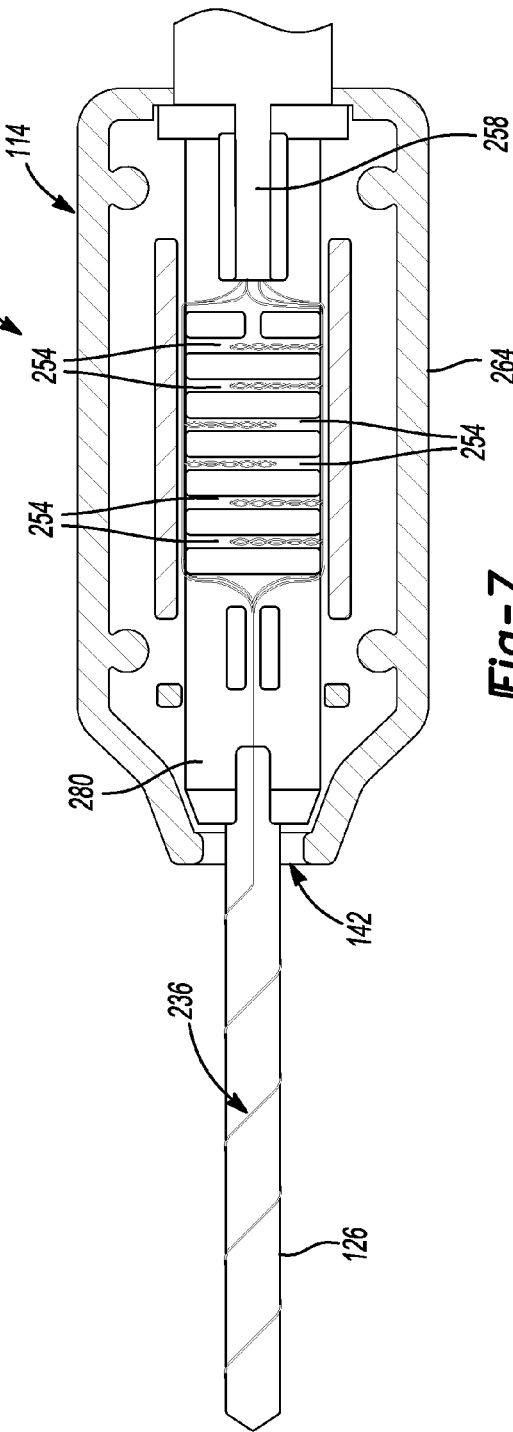
FIG. 7 is a partial view of a handle portion of the exemplary suction instrument according to the principles of the present disclosure.

Once the second set of wires 236 has been helically wound around the outside of tubular body 126 to the first end 142, the wires can be routed into slots 254 in handle assembly 114 and connected to respective lead wires of a cable connector assembly 258, as generally shown in FIG. 7. The cable connector assembly 258 can be connected to the navigation probe interface 80, as generally shown in FIG. 1. The handle assemble 114 can include two half sections 264, with one half section being shown in FIG. 7 for illustration purposes.

With particular reference to FIG. 6 and continued reference to FIGS. 2-5A, 7 and 10, the tube assembly 110 can include a polymeric outer heat shrink 272 covering the entire assembly, as shown in the cross-sectional view of FIG. 6. Thus, the heat shrink 272 can cover the elongated body 126, the insert portion 130, and the sensor arrangement 118 including the wires helically wound along the body 126. The heat shrink 272 can provide an outer covering or shell over the tube assembly 110 and sensor arrangement 118 while providing sufficient flexibility for both bending of the body 126 and slight relative movement of the helically wound wires 236 as a result of the bending. In this regard, the wires can be moveably captured between the heat shrink and the tubular body. The heat shrink covering can also serve as an electric isolation barrier. It should be appreciated that while the heat shrink covering is only shown in FIG. 6, it has not been shown in the other various views for clarification purposes only to better illustrate the sensor arrangement 118 and routing of wires 236. In this regard, it should be understood that the heat shrink 272 can cover the tube assembly 110 and sensor arrangement 118 shown in FIGS. 2-10.

As discussed above, the handle assembly 114 can include multiple components, such as for example two halves, with one of the halves shown in FIG. 7 receiving the first end of the suction tube assembly 110 in fluid communication with a suction passage 280 formed therein. The suction passage 280 can terminate at a connector 284 protruding from a proximal end of the handle (FIGS. 2 and 3) and can be configured to receive a suction hose or other arrangement in fluid communication with a suction source (not shown). Once the wires are connected to the cable assembly and routed in the slots 254 as discussed above, the other half of handle assembly 114 can connected and an adhesive can be used to bond the handle halves together to form the handle as shown in FIGS. 2 and 3.

With particular reference to FIG. 2, handle assembly 114 can include a suction adjustment feature 290 which can be in the form of a bore 292 extending from an outer surface 294 of the handle assembly 114 and into fluid communication with the suction passage 280. In operation, a surgeon or user 50 of the instrument 100 can place their thumb or another object over the bore 292 to vary an opening of the bore 292 and thus vary an amount of suction pressure realized in the flow path or passage 166. For example, if the bore 292 is left completely open or uncovered, a majority if not all of the suction will be through the bore 292 and not the first end 172 of insert portion 130. On the other hand, if the bore 192 is completely covered or closed off, a maximum amount of suction will be realized at end 172. Varying the opening of bore 292 between fully closed and fully opened can therefore correspondingly vary an amount of realized suction at end 172.

Figure 10:
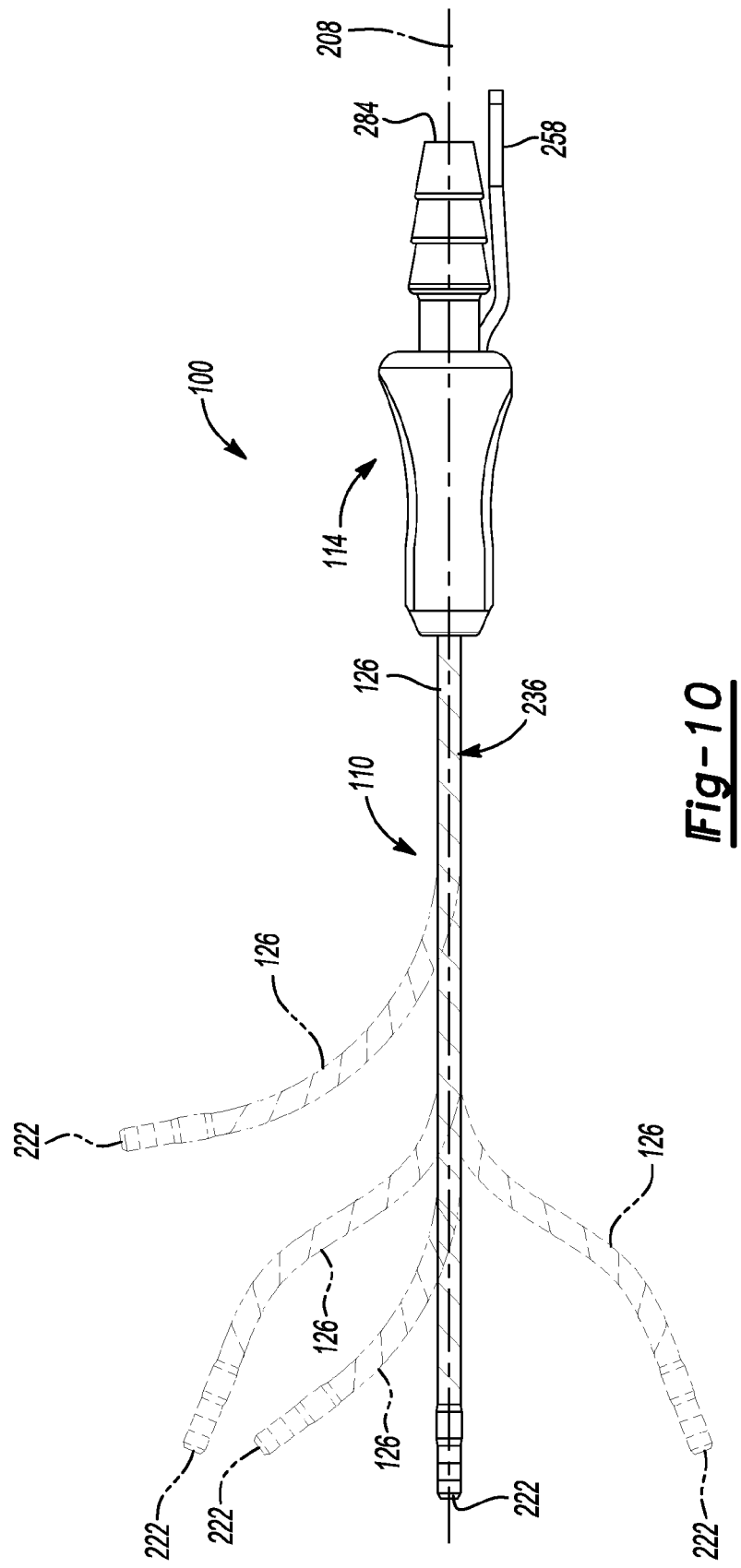
FIG. 10 is a view of exemplary bent or formed configurations of the exemplary malleable suction instrument according to the principles of the present disclosure.

In operation and with additional reference to FIG. 10, the malleable elongated body 126 can be bent into various configurations, as generally shown by the exemplary configurations 300A-D. The malleable nature of body 126 can provide the ability for body 126 to be bent into such various configurations without kinking and can maintain the various configurations until bent or shaped into another configuration. Further, malleable body 126 can be bent or shaped as discussed above without require additional tools, such as a mandrel to facilitate the bending. This is advantageous, for example, in that a surgeon can bend body 126 multiple times by hand during a procedure in close proximity to the patient without having to resort to additional tools or other equipment to facilitate the bending while performing the procedure.

Moreover, the helically wound configuration of wires 236 along with the Teflon coating provides for the ability to bend malleable body 126 at various angles including through ninety degrees without breaking the wires. More specifically, by winding wires 236 helically around body 126 at an angle relative to the longitudinal axis and at a close proximity to each other, the wound wires can conform to the bent shape and move or flex axially with the bent tube such that they do not strain and/or break during the bending. In addition, the Teflon coating provides added lubricity for the wires to have relative motion between the tube and the outer shrink coating 272 during bending.

Further, by providing the tracking device 84 near the distal tip 222, the distal tip 222 of the suction instrument can be tracked to provide substantially accurate position data for the distal tip of suction instrument 100 when out of a line of sight in a body cavity of patient 34. This is particularly useful for the malleable suction instrument 100 because, for example, the tip can be bent or moved relative to the handle and still be tracked. On the other hand, if the tracking device was in the handle (such as in a hind tracked system) and the body 126 was subsequently bent or shaped, the navigation system would no longer be able to accurately track the position of the distal tip. In this regard, the present teaching provide a tip tracked malleable suction instrument that can be bent or shaped into various configurations as may be required during a procedure, and the distal tip can be accurately tracked in any of the various bent positions.

In use, the patient 34 can be positioned on an operating table or other appropriate structure and appropriate image data of a patient or navigation space can be obtained, such as an ENT area. The image data can be registered to the navigation space as is known in the art. The surgeon 50 can determine a shape of the malleable suction instrument 100 to reach a target site and bend the suction instrument 100 to the determined shape where instrument 100 retains the bent shape, as discussed above. The bent or shaped surgical instrument 100 can then be guided to the target site with crosshairs representing the position of the distal tip of instrument 100 being superimposed on the image data. The crosshairs can show the tracked relative position of the distal tip as instrument 100 is navigated to the target site. In addition, if during navigation of the shaped instrument 100 to the target site, the surgeon determines that the shaped configuration will need to be altered, the surgeon can bend and/or reshape the instrument 100 to a newly shaped configuration and proceed again as discussed above.

Figure 11:
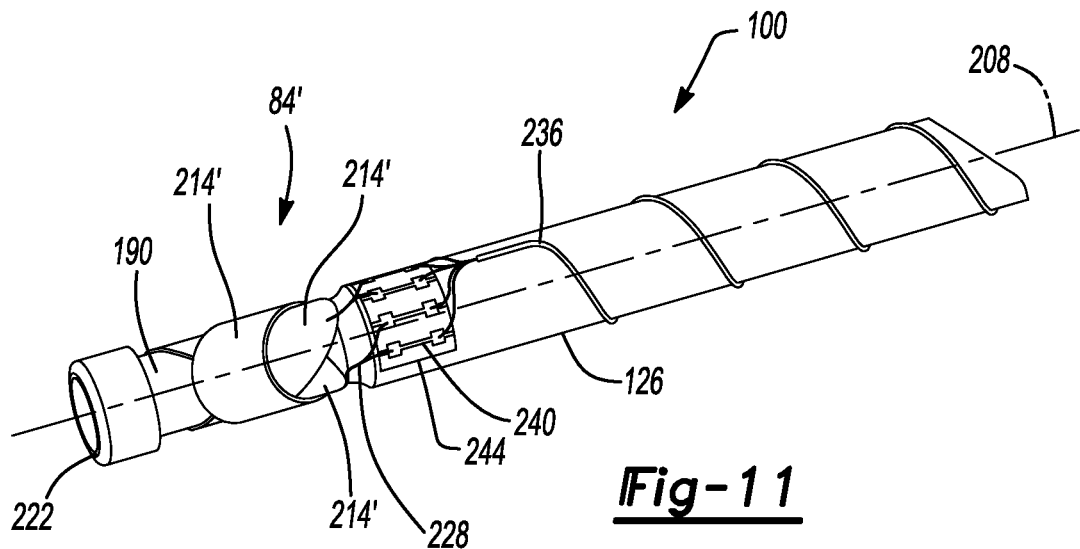
FIG. 11 is a partial perspective view of the distal region of the exemplary suction instrument illustrating an exemplary alternative tracking arrangement associated with the exemplary flexible circuit sheet according to the principles of the present disclosure.

With additional reference to FIG. 11, an alternative tracking device arrangement 84' will now be discussed. As can be seen in FIG. 11, tracking device 84' can include two or three wrapped coil assemblies 214' that can be used in place of the coil assemblies 214. Coil assemblies 214' can be wrapped around sleeve 190 proximate the distal tip 222. In one exemplary configuration, the coil assemblies 214' can be individually wrapped around sleeve 190 in an overlapping manner with a wrap axis having a non-normal and non-parallel angle to longitudinal axis 208. In the exemplary configuration illustrated, coil assemblies 214' can be wrapped around sleeve 190 at an angle relative to each other and longitudinal axis 208. In another exemplary configuration, coil assemblies 214' can be wrapped around sleeve 190 and spaced axially apart from each other. A further discussion of the coil assemblies 214' can be found in U.S. application Ser. No. 12/770,181, filed on Apr. 29, 2010 and entitled "Method and Apparatus for Surgical Navigation", the disclosure of which is incorporated by reference herein in its entirety.

Figure 12:
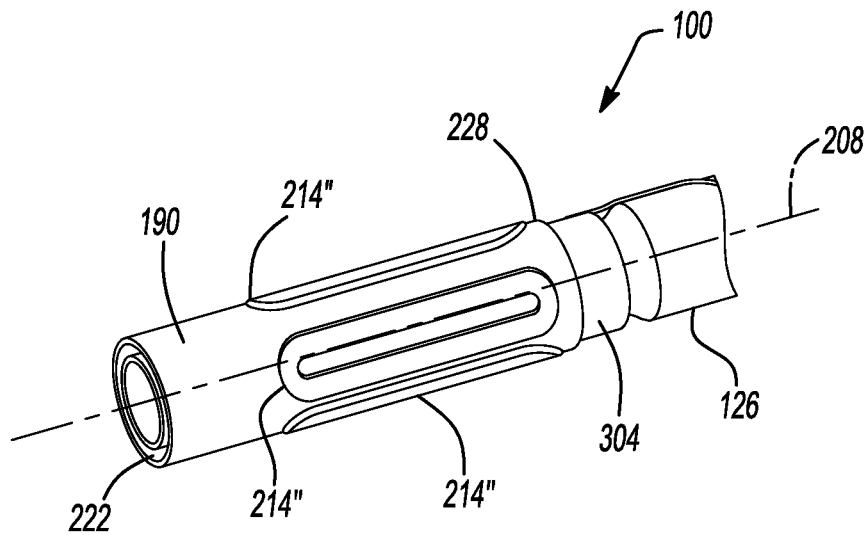
FIG. 12 is a partial perspective view of the distal region of the exemplary suction instrument illustrating another exemplary alternative tracking arrangement according to the principles of the present disclosure.

With additional reference to FIG. 12, another alternative tracking device arrangement 84" is shown associated with instrument 100. Tracking device 84" can also be used in place of tracking device 84 and can include a plurality of oval coil assemblies 214" positioned about sleeve 190 proximate distal tip 222. In one exemplary configuration, two to four coil assemblies 214" can be positioned about sleeve 190 proximate distal tip 222. In the exemplary configuration illustrated, four coil assemblies 214" can be circumferentially spaced around sleeve 190 proximate distal tip 222, and an axial coil 304 can be positioned proximally of coil assemblies 214", as shown in FIG. 12. In one exemplary configuration, two oval coil assemblies 214" can be provided with the axial coil 304. The two coil assemblies 214" can also include two pair of coil assemblies 214" provided with the axial coil 304.

The coil assemblies 214" can be formed in various selected shapes, such as elliptical, circular, or oval. In one exemplary configuration, the axial coil 304 can be concentric with and wrapped around an outer surface of sleeve 190 or body 126, as shown in FIG. 12. A further discussion of coil assemblies 214" and axial coil 304 can be found in U.S. application Ser. No. 13/016,740, filed on Jan. 28, 2011 and entitled "Method and Apparatus for Image-Based Navgation", the disclosure of which is incorporated by reference herein in its entirety.

Figure 13A:
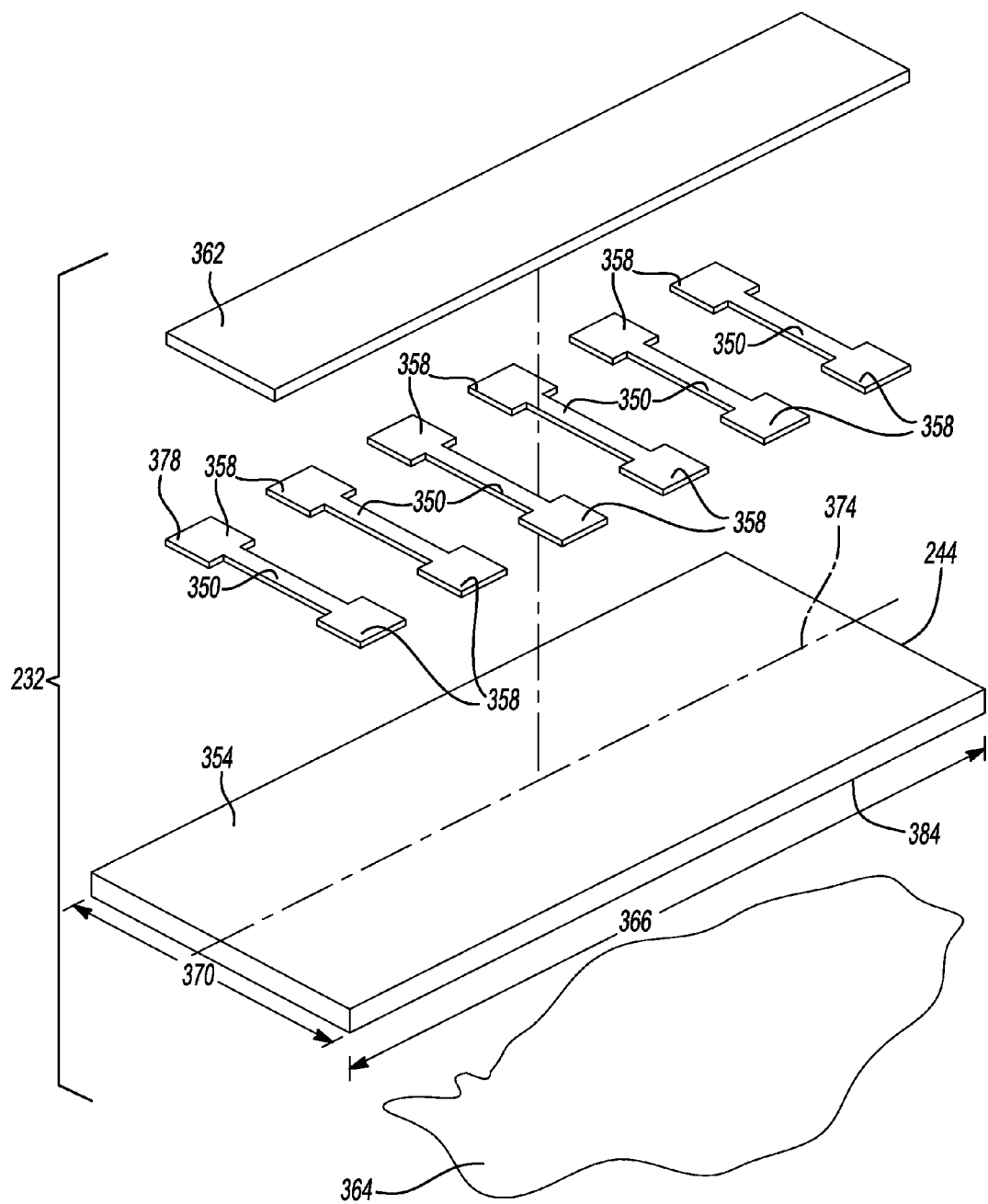
FIG. 13A is an exploded perspective view of an exemplary configuration of the flexible printed circuit sheet according to the principles of the present disclosure.

Turning now to FIGS. 13A-18, the flexible printed circuit sheet 232, including various exemplary configurations thereof, will now be discussed in greater detail. With particular reference to FIGS. 13A-13B, one exemplary configuration of the flexible printed circuit sheet 232 is shown in both an exploded view (FIG. 13A) and an assembled view (FIG. 13B). Flexible printed circuit sheet 232 can include the flexible backing or base layer 244, one or more circuit or conductive traces, such as copper traces 350, positioned on a first or upper side 354 of base layer 244, circuit pads 358 associated with traces 350, and an insulative layer 362 formed over at least the copper traces 350 and coupled to base layer 244. It will be appreciated that while copper traces 350 are shown positioned on upper side 354, the copper traces 350 can also be positioned on an opposite lower side of base layer 244. While the discussion will continue with reference to the conductive traces being copper traces 350, the conductive traces can also be formed from metal, nickel, gold, or copper with nickel/gold plating.

The flexible printed circuit sheet 232 can provide a mechanism for facilitating fine gauge wire termination of associated sensors or coils and lead wires, such as wires 228 and 236 of exemplary suction instrument 100. The flexible printed circuit sheet 232 can also enable manufacturing and design flexibility in connection with use of circuit sheet 232 on instruments and other devices that are flexible and/or conformable. For example, conventional techniques for electrically terminating sensor wires to lead wires can include directly connecting the sensor wires to the lead wires via soldering. As can be appreciated, such a technique is very time and labor intensive considering that the sensor and lead wires can include 58 AWG wire with an outer diameter of approximately 0.01 mm. Indeed, such conventional techniques for soldering the sensor wires to the lead wires often require performing the process under a microscope or other magnifying apparatus, which can further drive cost and expense into the manufacturing process.

As will also be discussed in greater detail below, the exemplary flexible circuit sheets discussed herein can provide for improved efficiency and cost reduction in terminating such fine gauge sensor and lead wires, especially for medical instruments having size or volume constraints and that also require flexibility or conformability. In this regard, the circuit pads 358 on the flexible circuit sheet 232 can be orders of magnitude bigger than the outer diameter of the wires to be terminated, such as a 0.1 mm to 0.5 mm square pad, for example. In an exemplary configuration, the circuit pads 358 can have a large surface area for the wires to be terminated such that, for example, a primary linear dimension of the circuit pads 358 can be orders of magnitude bigger than the outer diameter of the wires to be terminated. In one exemplary configuration, the wires to be terminated can include an outer diameter of between approximately 0.03 mm to 0.05 mm. In an exemplary configuration, the wires to be terminated can include 58 AWG wire having an outer diameter of approximately 0.01 mm. This can, among other things, facilitate easier and more efficient termination of the fine gauge wire due to the larger size of circuit pads 358.

The base layer 244 can be formed form various materials having appropriate insulative properties and appropriate material properties such that base layer 244 is flexible and can conform to various surface geometries. For example, the base layer 244 (as well as the assembled printed circuit sheet 232) can conform to the outer tubular surface of the malleable suction instrument 100. In one exemplary configuration, the flexible nature of flexible circuit sheet 232 can facilitate movement with tube assembly 110 of malleable instrument 100 (e.g., FIG. 10) once adhered thereto. In one exemplary configuration, the base layer 244 can be formed from a polymeric material, including but not limited to, a polyimide. In the exemplary configuration illustrated in FIGS. 13A-13B, the base layer 244 can include a length 366 of approximately 7 mm and a width 370 of approximately 3 mm. It should be appreciated, however, that the size and shape of base layer 244 can vary depending on a particular application.

The copper traces 350 can be positioned or printed in any desired orientation on base layer 244, including substantially perpendicular to a longitudinal axis 374 of base layer 244. The copper traces 350 can similarly include varying lengths and widths depending on the particular configuration of flexible printed circuit sheet 232. In the exemplary configuration illustrated in FIGS. 13A-13B, the copper traces 350 can include a length of approximately 1.25-3.0 mm and a width of approximately 0.15 mm. The copper traces 350 can include a thickness of approximately 0.01-0.04 mm.

Figure 13B:
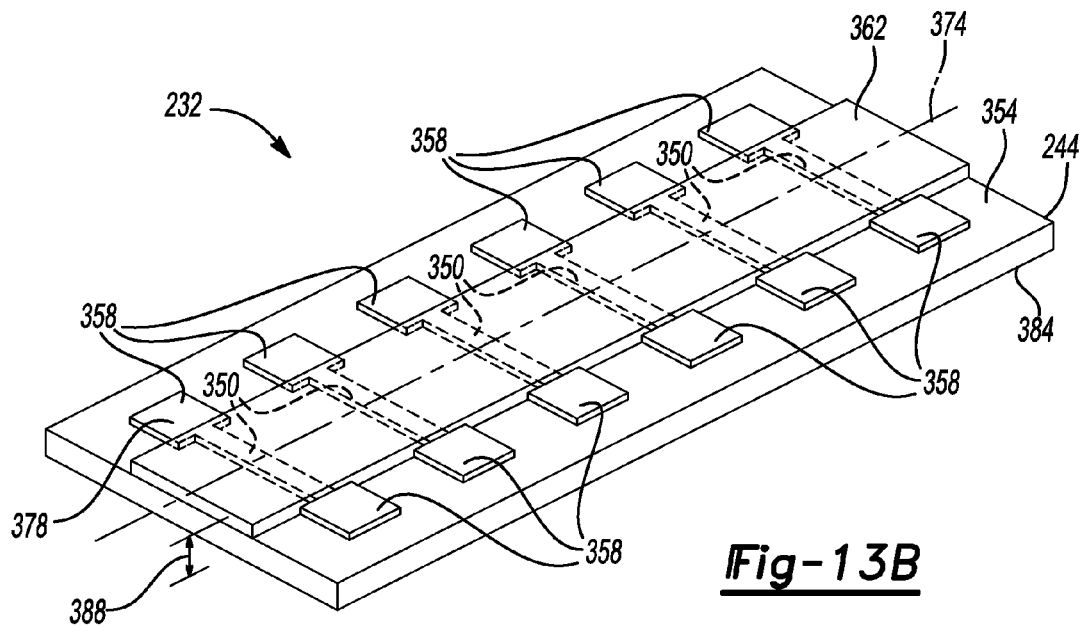
FIG. 13B is a perspective view of the flexible printed circuit sheet of FIG. 13A in an exemplary assembled configuration according to the principles of the present disclosure.

The circuit pads 358 can be positioned or printed at ends of the copper traces 350, as can be seen in FIGS. 13A-13B. The circuit pads 358 can be formed in any desired shape, including the square or substantially square shape 378 shown, for example, in FIGS. 13A-13B. The circuit pads 358 can also be formed to have varying dimensions, including a dimension or dimensions that is/are larger than a typical outer diameter of the wires that are to be coupled to the pads. As discussed above, such a greater dimension of the circuit pads 358 relative to the size of the wire can provide for easier soldering of the wires to the pads 358 and thus reduce time and manufacturing complexity associated with building an instrument requiring termination of fine gauge wires.

For example, the exemplary circuit pads 358 shown in FIGS. 13A-13B are square in shape and include a length and width of approximately 0.5 mm. Again, it should be appreciated that the length and width of circuit pads 358 can vary depending on the particular application of flexible printed circuit sheet 232. The circuit pads 358 can also be formed from copper and include a tinning material, such as tin/lead, nickel/gold and/or gold.

The insulative layer 362 can be positioned over the copper traces 350 and coupled to the base layer 244 in any suitable manner that allows or does not inhibit the flexibility and conformability of the flexible circuit sheet 232. In one exemplary configuration, the insulative layer 362 can be adhered to the base layer 244 and copper traces 350 with an adhesive. The insulative layer 362 can include a shape and/or width so as to cover or substantially cover the copper traces 350 between the circuit pads 358 to insulate the traces 350 from external contact. Similar to the base layer 244, the insulative layer 362 can also be formed from a polymeric material, such as polyimide. In one exemplary configuration, the insulative layer 362 can be a photoimageable coverlay. As will be discussed in greater detail below, the insulative layer 362 can include a thickness that is less than a thickness of the base layer 244. In the exemplary configuration shown in FIGS. 13A-13B, the insulative layer 362 can include a rectangular shape corresponding to the exemplary symmetrical positioning of the copper traces 350 and corresponding circuit pads 358.

To couple the flexible printed circuit sheet 232 to a structure, such as the exemplary instrument 100, an adhesive 364 can be used. It should be appreciated, however, that other means for securing the flexible circuit sheet 232 to a structure can be used, so long as the means used does not inhibit the flexible nature of printed circuit sheet 232. In one exemplary configuration, the adhesive 364 can be applied to a lower or second side 384 of base layer 244. In this regard, the second side of base layer 244 can be substantially smooth. It should also be appreciated that the adhesive 364 can also be applied to the structure in addition to or in lieu of being applied to base layer 244. In one exemplary configuration, the adhesive 364 can include a medical grade pressure sensitive adhesive. In another exemplary configuration, the adhesive 364 can include a medical grade liquid or gel adhesive.

The exemplary flexible printed circuit sheet 232, in the exemplary assembled configuration shown in FIG. 13B, can include a bound together or overall thickness 388 of between approximately 0.04-0.07 mm. In some exemplary embodiments, the overall thickness 388 can be only approximately 0.04 mm. Stated another way, the assembled base layer 244, circuit traces and pads 350, 358 and insulative layer 263 can include an overall thickness 388 of approximately 0.05 mm. It should be appreciated, however, that such a thickness can vary to be smaller or larger depending on the particular application of the flexible printed circuit sheet 232. Use of the pressure sensitive adhesive 364 can increase the overall thickness 388 by approximately 0.025 mm to 0.05 mm. Similarly, use of the gel or liquid adhesive can increase the thickness 388 by only 0.01 mm. Thus, the overall thickness 388 of the flexible printed circuit sheet 232, in various different configurations, can vary from 0.04 mm (without adhesive 364) to approximately 0.11 mm (with adhesive 364). As discussed above, such a minimal thickness 388 of flexible circuit sheet 232 provides for not only flexibility and conformability of the circuit sheet 232, but also applicability of the flexible circuit sheets to medical and other devices and/or instruments that have very tight volume and/or packaging constraints.

For example, one of ordinary skill in the art will appreciate that conventional printed circuit boards considered thin in the industry can include a thickness of 0.8 mm or greater and can be made from dielectric layers laminated together with epoxy resin prepreg. Such materials combined with such a thickness do not provide for the conventional circuit boards being flexible and thus they cannot conform to non-planar surfaces and/or flex such that they cannot be used with a flexible or malleable medical instrument. Further, such a thickness of 0.8 mm or greater can preclude use of conventional printed circuit boards in medical instruments or devices where maintaining a minimum thickness or overall height is a critical parameter.

The very thin thickness 388 of the exemplary flexible circuit sheet 232, together with the polyimide material construction, can provide for significant flexibility and/or conformability of circuit sheet 232. In this regard, the exemplary flexible circuit sheet 232 having the overall thickness 388 and polyimide material construction can include a bend radius of approximately ten times the thickness 388. Thus, for the exemplary configuration of flexible circuit sheet 232 discussed herein, the bend radius can be approximately 0.4 mm to 0.7 mm depending on the overall thickness 388 of the flexible printed circuit sheet 232. Such a bend radius can provide for significant flexibility in conforming the flexible printed circuit sheet to or around tight radii associated with compact or low profile medical instruments or devices.

Figure 14:
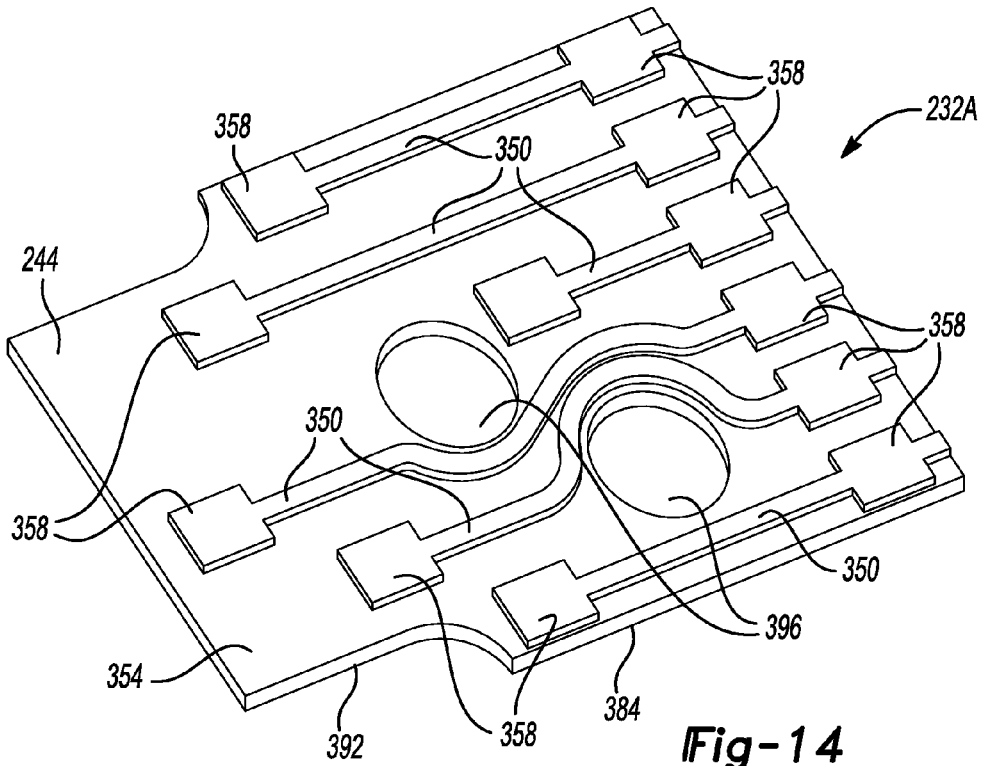
FIG. 14 is a perspective view of another exemplary flexible printed circuit sheet according to the principles of the present disclosure.

With additional reference to FIGS. 14-16, another exemplary flexible printed circuit sheet 232 will now be discussed and designated with reference numeral 232A. Flexible printed circuit sheet 232A can include similar properties and thickness dimensions as discussed above for flexible circuit sheet 232 such that like reference numerals refer to like features or components. Flexible printed circuit sheet 232A is shown having an exemplary custom shape 392 configured for a particular medical instrument or device. In the exemplary configuration illustrated in FIGS. 14-16, flexible printed circuit sheet 232A can include one or more apertures 396 configured to be positioned around and/or provide access to corresponding coil assemblies 214. The copper circuit traces 350 can be printed in various patterns to accommodate the apertures 396 and custom shape 392, as shown for example in FIG. 14. It should be appreciated that while not shown for clarity purposes, the insulative layer 362 can be custom shaped to include appropriate cutouts and an appropriate shape to cover the copper traces 350 while leaving the circuit pads 358 of flexible circuit sheet 232A exposed.

Figure 15:
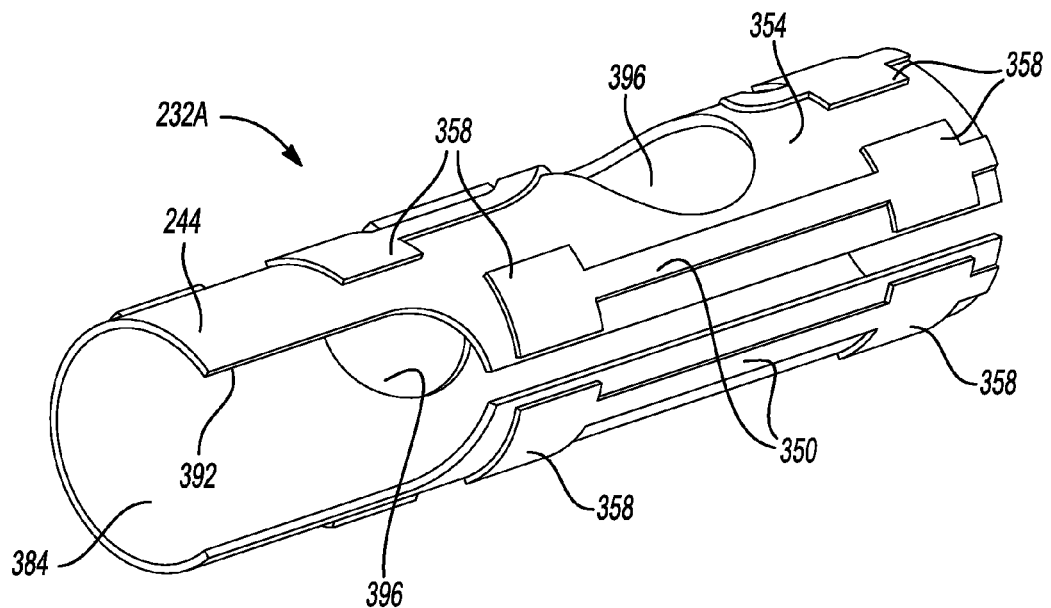
FIG. 15 is a perspective view illustrating the flexible printed circuit sheet of FIG. 14 in a bent or flexed condition according to the principles of the present disclosure.
Figure 16:
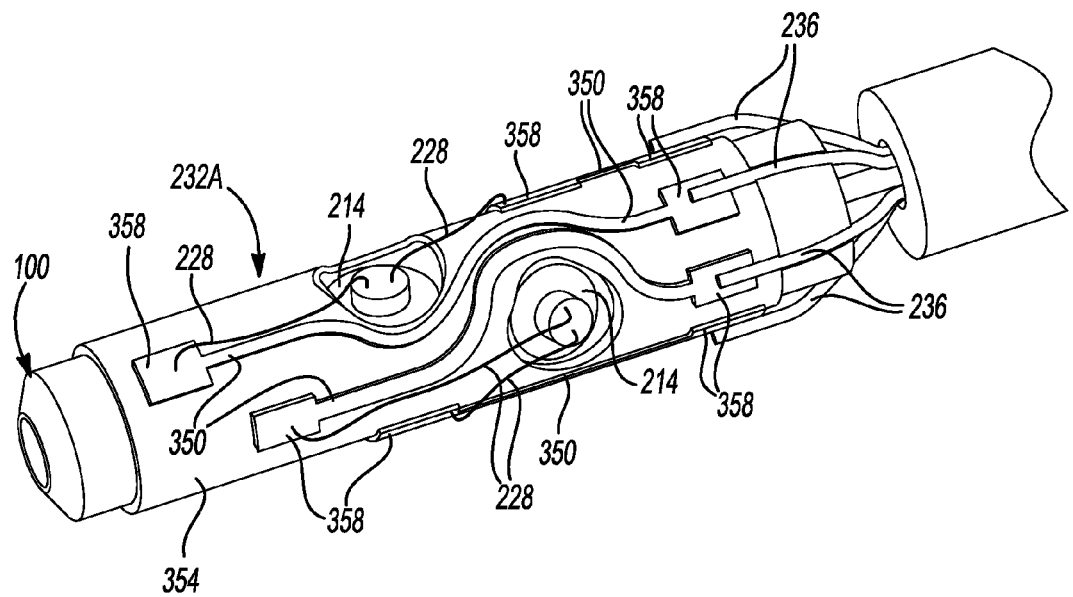
FIG. 16 is a perspective view of the flexible printed circuit sheet of FIGS. 14 and 15 in a flexed condition conforming to an outer surface of an exemplary instrument according to the principles of the present disclosure.

As can be seen in FIGS. 15-16, the flexible printed circuit sheet 232A can be bent or flexed in various configurations to conform to various instrument or device shapes, such as the distal end of a malleable suction instrument 100. In one exemplary configuration, the flexible printed circuit sheet 232A can wrap around or substantially around the malleable suction instrument 100. The flexible printed circuit sheet 232A can also bend, flex or twist with the malleable suction instrument 100 during use thereof. In this regard, the flexible printed circuit sheet 232A can flex three-dimensionally. In the exemplary configuration shown in FIG. 16, flexible circuit sheet 232A can be adhered to the outer surface of a component of malleable suction instrument 100 using, for example, adhesive 364. As discussed above, the lead wires 236A can be electrically coupled, such as via soldering, to the appropriate circuit pads 358 and the coil assembly wires 228 can be soldered to the corresponding pads 358, as also shown in FIG. 16.

Figure 17:
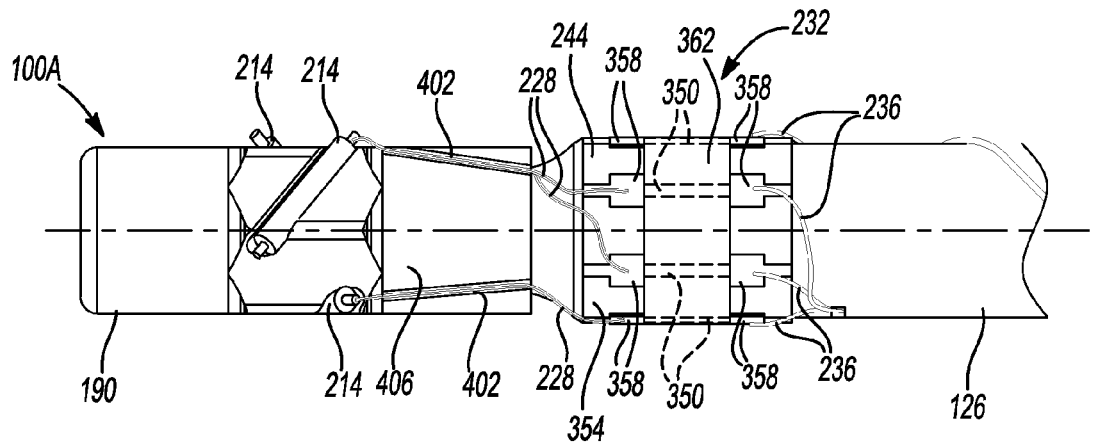
FIG. 17 is a partial side view of the distal region of the exemplary suction instrument of FIG. 5 associated with the exemplary flexible circuit sheet and having wire management channels according to the principles of the present disclosure.

Turning now to FIG. 17, flexible printed circuit sheet 232 is shown adhered to malleable suction instrument 100A, which is substantially similar to malleable suction instrument 100 shown in FIG. 5, except for channels 402 formed in sleeve 190. Channels 402 can receive sensor or coil wires 228 and provide a predetermined routing placement for wires 228 relative to instrument 100A, as well as position wires 228 below an outer surface 406 of sleeve 190. Flexible printed circuit sheet 232 can conform to an outer surface of malleable suction instrument 100A and can provide for efficient and cost effective termination of coil assembly wires 228 and lead wires 236, as shown for example in FIG. 17. For example, flexible circuit sheet 232 can be flexed to correspond to a radius of the outer surface of the instrument so as to lay substantially flush or coplanar to the outer surface.

Figure 18:
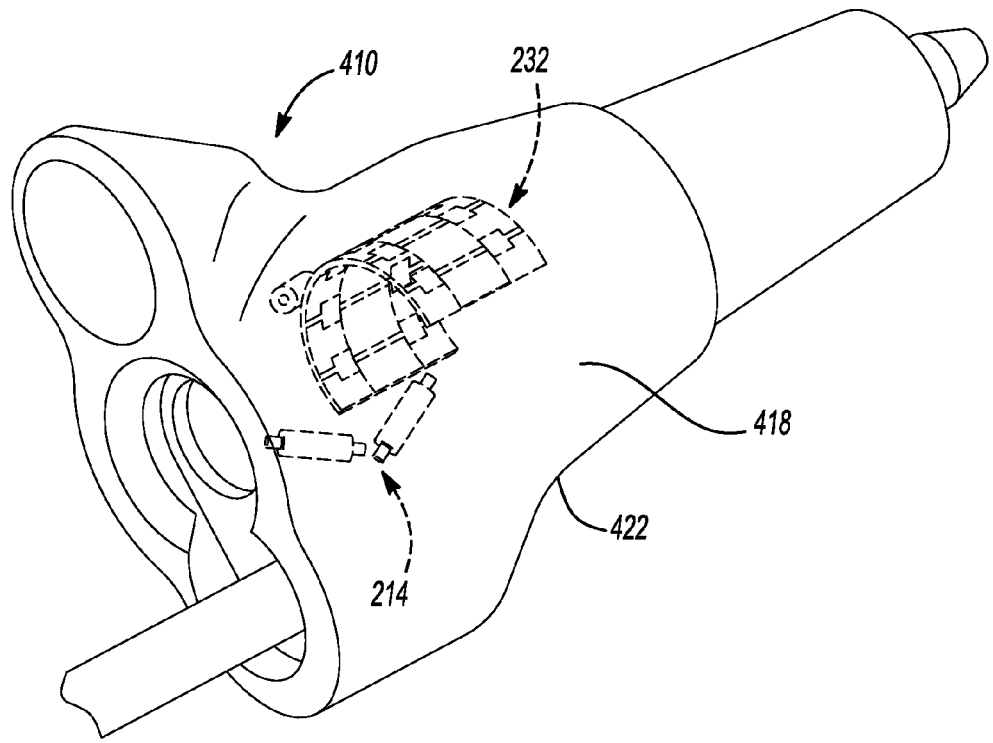
FIG. 18 is a perspective view of a patient tracking device having an exemplary flexible printed circuit sheet and associated coils according to the principles of the present disclosure.

With particular reference to FIG. 18, flexible printed circuit sheet 232 is shown associated with an electromagnetic patient tracker device 410. In the exemplary configuration illustrated, tracker device 410 can include the three coil assemblies 214 positioned equidistant circumferentially around a longitudinal axis 414 of tracker device 410 and can be configured to communicate with and be tracked by EM tracking system 60 of navigation system 10. The coils assemblies 214 can also be positioned, in the exemplary configuration illustrated, at an angle, such as between forty-five degrees and fifty-five degrees relative to axis 414 in a similar manner as coil assemblies 214 are positioned relative to instrument 100 shown in FIG. 5. It will be appreciated, however, that various other coil assembly configurations and/or orientations can be utilized with patient tracker 410.

The flexible printed circuit sheet 232 can be positioned inside of or within a body 418 of tracker 410 as shown in FIG. 18, or could alternatively be positioned on an outer surface 422 of tracker 410. In one exemplary configuration, flexible printed circuit sheet 232 can be bent or flexed to conform to the shape or contour of the surface it will be adhered to, as shown in FIG. 18. Sensor and lead wires (not shown for clarity) can be soldered to the respective circuit pads in the manner discussed above.

Turning now to FIGS. 19 and 20A-20C, another exemplary configuration of a flexible printed circuit sheet is shown at 232B. Flexible printed circuit sheet 232B can be similar to flexible printed circuit sheet 232A such that like reference numerals refer to like components or features and only differences will be discussed in detail. Similar to flexible printed circuit sheet 232A, the flexible printed circuit sheet 232B can include base layer 244 having upper surface 354, conductive traces 350, solder or circuit pads 358 and top insulative layer 362.

Figure 19:
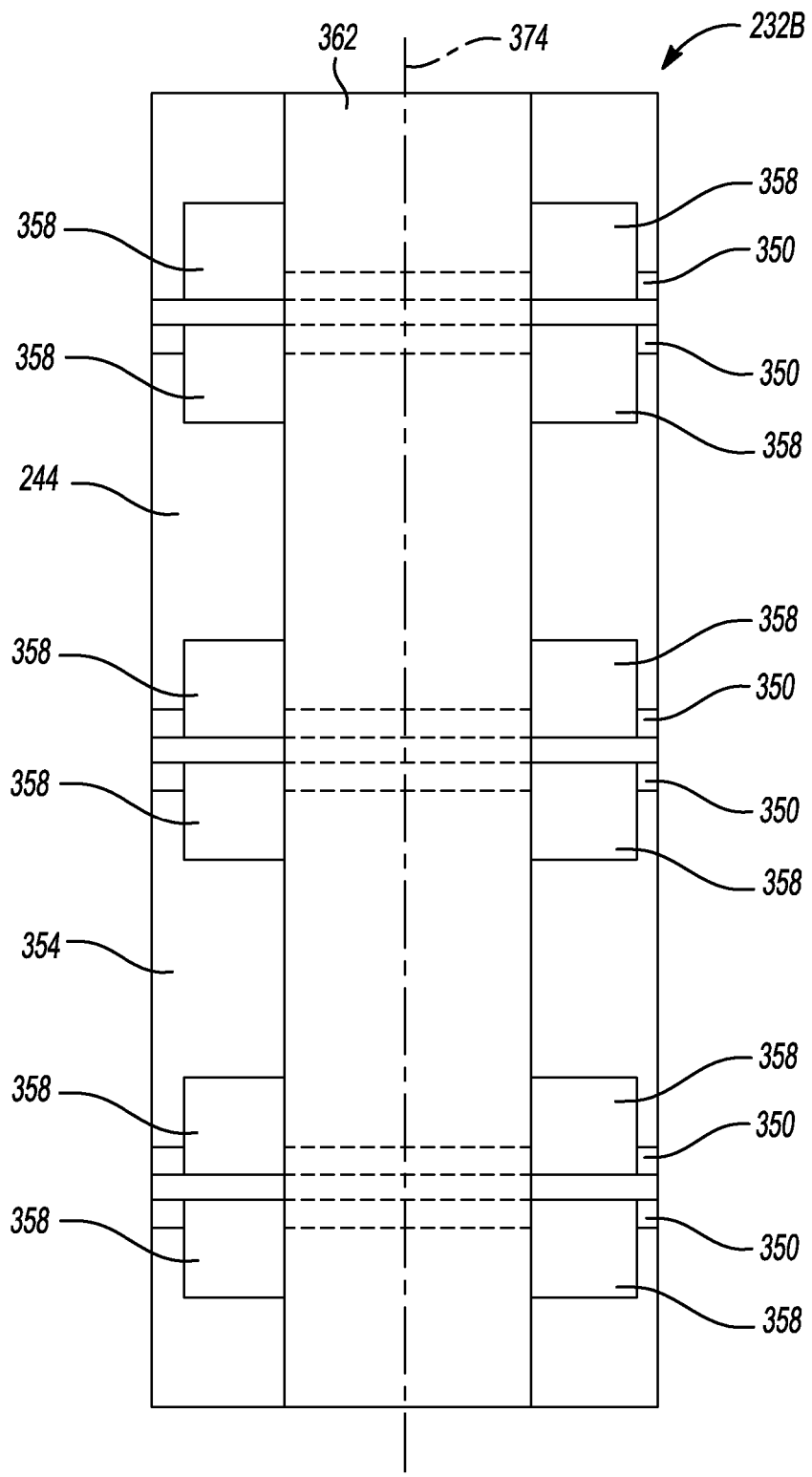
FIG. 19 is a top view of another exemplary flexible printed sheet according to the principles of the present disclosure.

The flexible printed circuit sheet 232B can include one or more paired circuit traces where the pairs of circuit traces are closely spaced together, as shown for example in FIG. 19. By positioning the circuit traces in such a manner along the longitudinal axis 374, any electromagnetic interference and/or pickup from an associated electromagnetic navigation system can be minimized. In this exemplary configuration, the conductive traces 350 can be parallel or substantially parallel to each other and spaced apart by less than 0.3 mm, including 0.23 mm, in each pair of circuit traces. However, it should be appreciated that other spacing may be utilized depending on design and other variables.

Figure 20A:
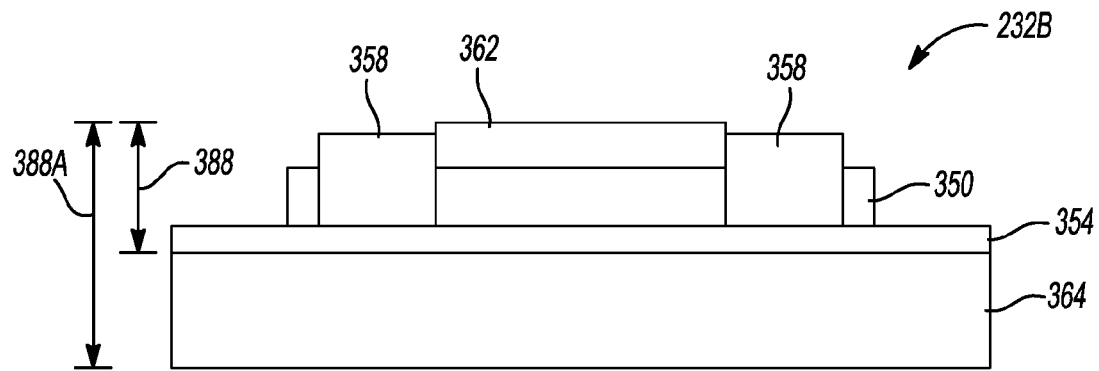
FIGS. 20A-20C are side views representing various exemplary configurations of the flexible printed circuit sheet of FIG. 19 according to the principles of the present disclosure.
Figure 20B:
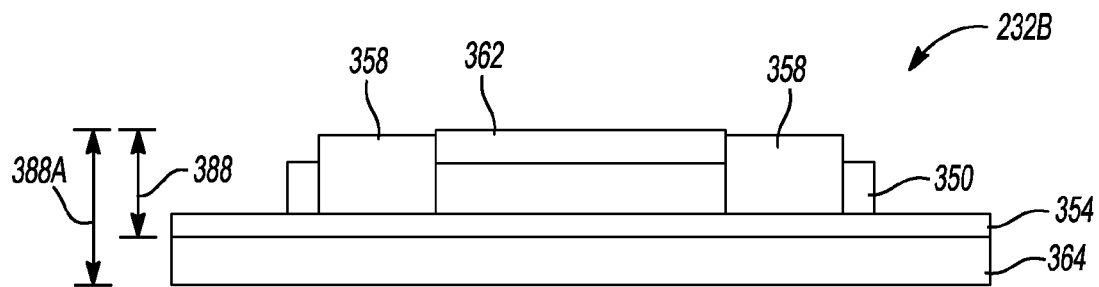
Figure 20C:
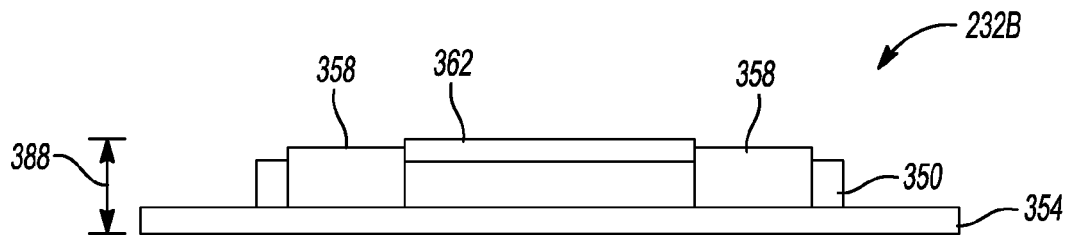

With particular reference to FIGS. 20A-20C, three exemplary configurations (shown in side views) of the flexible printed circuit sheet 232B are shown. In these exemplary configurations, various different thicknesses of the flexible printed circuit sheet 232B are shown with and without adhesive, as will be discussed in greater detail below.

Referring to FIG. 20A, flexible printed circuit sheet 232B is shown in a configuration utilizing adhesive 364. In this configuration, the base layer 244 can include a thickness of approximately 0.01 mm, the conductive traces and pads 350, 358 can include a thickness of approximately 0.04 mm and the insulative layer 362 can include a thickness of approximately 0.02 mm. In the assembled configuration, the flexible printed circuit sheet 232B shown in FIG. 20A can include an overall thickness 388 of approximately 0.07 mm without adhesive 364 and an overall thickness 388A of 0.11 mm with adhesive 364.

With reference to FIG. 20B, the flexible printed circuit sheet 232B is shown having a smaller overall thickness 388 of approximately 0.05 mm without adhesive 364 and an overall thickness 388A of 0.07 mm with adhesive 364. In this configuration, the base layer 244 can similarly have a thickness of approximately 0.01 mm, the conductive traces and pads 350, 358 can include a thickness of approximately 0.02-0.03 mm and the insulative layer can include a thickness of approximately 0.01 mm.

Referring now to FIG. 20C, the flexible printed circuit sheet 232B is shown in another exemplary configuration having an overall thickness 388 of approximately 0.04 mm. In this configuration, adhesive 364 may not be utilized. In such a configuration where adhesive 364 is not utilized, a heat shrink layer over the flexible printed circuit sheet 232B can optionally be utilized to couple flexible printed circuit sheet 232B to an instrument, such as the suction instrument 100 discussed above. In this configuration of flexible printed circuit sheet 232B, the base layer 244 can also include a thickness of approximately 0.01 mm, the conductive traces and pads 350, 358 can include a thickness of approximately 0.01-0.02 mm and the insulative layer 364 can include a thickness of approximately 0.01 mm.

It will be appreciated that while various configurations of flexible printed circuit sheets have been discussed herein, other configurations can be utilized taking advantage of the thin, compact and conformable features of such flexible printed circuit sheets. For example, as an alternative to helically winding the lead wires 236 along body 126 of tube assembly 110, as shown for example in FIG. 5, a flexible printed circuit sheet having the properties discussed herein could be sized and shaped for winding along body 126 in a similar manner to the lead wires 236. In this exemplary configuration, such a flexible printed circuit sheet could include a length configured to be helically wound from the sleeve 190 to the handle assembly 114. The coil assembly wires 228 could then be soldered to the appropriate circuit pads adjacent sleeve 190 and the lead wires 236 could be soldered to the appropriate circuit pads 358 adjacent handle assembly 114, thereby eliminating a need to route lead wires along body 126.

While one or more specific examples have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

What is claimed is:

1. A flexible circuit assembly for a navigated medical instrument, the flexible circuit assembly comprising:
   a base layer;
   a plurality of pads applied to the base layer, wherein the plurality of pads comprise first pads and second pads;
   a plurality of traces formed on a first side of the base layer and connecting the first pads to the second pads;
   a plurality of wires; and
   an insulative layer formed over the plurality of traces between the first pads and the second pads to isolate the circuit traces from an external environment,
   wherein
      the base layer and the insulative layer have material properties and a thickness, such that the base layer and the insulative layer are configured to facilitate flexing of the flexible circuit assembly to allow the flexible circuit assembly to conform to a non-planar surface of the navigated medical instrument,
      the base layer comprises an aperture,
      the aperture is adapted to provide access to a tracking device,
      the tracking device comprises a coil,
      a portion of the tracking device is disposed within the aperture, and
      the plurality of wires connect two of the second pads to the tracking device, wherein the plurality of wires are connected to (i) the two of the second pads outside of the aperture, and (ii) the tracking device within the aperture.

2. The flexible circuit assembly of claim 1, wherein the flexible circuit assembly has a thickness of approximately 0.05 mm.

3. The flexible circuit assembly of claim 2, wherein the flexible circuit assembly has a thickness of 0.04 mm.

4. The flexible circuit assembly of claim 3, wherein the flexible circuit assembly has a bend radius of 0.4 mm.

5. The flexible circuit assembly of claim 1, wherein the base layer and the insulative layer are formed from polyimide or a photoimageable coverlay.

6. The flexible circuit assembly of claim 1, further comprising an adhesive layer in contact with a second side of the base layer and adapted to adhere the flexible circuit assembly to the navigated medical instrument.

7. The flexible circuit assembly of claim 6, wherein the adhesive layer includes a pressure sensitive adhesive material.

8. The flexible circuit assembly of claim 6, wherein a thickness of the flexible circuit assembly is 0.07-0.11 mm.

9. The flexible circuit assembly of claim 8, wherein a thickness of the flexible circuit assembly is 0.07 mm.

10. The flexible circuit assembly of claim 1, further comprising the navigated medical instrument,
   assembly is in a tubular configuration to conform to the non-planar surface of the navigated medical instrument and is adhered to the non-planar surface via an adhesive material.

11. The flexible circuit assembly of claim 1, wherein the insulative layer is not formed over the plurality of pads.

12. A flexible circuit assembly for a navigated medical instrument, the flexible circuit assembly comprising:
a base layer;
a plurality of pads;
a plurality of wires;
a plurality of traces, wherein each of the plurality of traces is coupled to a respective pair of the plurality of pads, wherein the plurality of traces are formed on a first side of the base layer, and wherein
the base layer comprises a first aperture;
the first aperture is adapted to provide access to a first tracking device, wherein a portion of the first tracking device is disposed within the first aperture, and wherein the first tracking device comprises a coil, and
the plurality of wires connect two of the pads to the first tracking device, wherein the plurality of wires are connected to (i) the two of the pads outside of the first aperture, and (ii) the first tracking device within the first aperture; and
an insulative layer formed over the plurality of traces to isolate the plurality of traces from an external environment, and
flexible circuit assembly has material properties that facilitate the flexible circuit assembly conforming to a non-planar surface of the navigated medical instrument.

13. The flexible circuit assembly of claim 12, wherein:
the base layer and the insulative layer are formed from polyimide; and
the flexible circuit assembly has an overall thickness of 0.04 mm.

14. The flexible circuit assembly of claim 13, wherein the flexible circuit assembly has a bend radius of 0.4 mm.

15. The flexible circuit assembly of claim 12, further comprising an adhesive layer (i) configured to contact a second side of the base layer, and (ii) adapted to adhere the flexible circuit assembly to the navigated medical instrument,
wherein the flexible circuit assembly has a thickness of 0.07-0.11 mm.

16. The flexible circuit assembly of claim 12, wherein:
the navigated medical instrument includes a malleable tube assembly;
wherein the flexible circuit assembly is in a tubular configuration to conform to the non-planar surface;
the malleable tube assembly includes the non-planar surface; and
the flexible circuit assembly is adhered to the non-planar surface with an adhesive material such that the flexible circuit assembly is configured to bend or flex with bending of the malleable tube assembly.

17. The flexible circuit assembly of claim 16, further comprising the first tracking device, wherein:
the base layer comprises a plurality of apertures;
the plurality of apertures comprises the first aperture;
the plurality of wires connect pairs of the pads to a plurality of tracking devices; and
the plurality of tracking devices include the first tracking device.

18. The flexible circuit assembly of claim 12, wherein the flexible circuit assembly has an overall thickness of 0.05 mm.

19. A navigated medical instrument comprising:
a flexible circuit assembly comprising
a base layer,
a first plurality of pads,
a second plurality of pads,
a plurality of traces, wherein each of the plurality of traces is coupled to a respective one of the first plurality of pads and a respective one of the second plurality of pads, and wherein the plurality of traces are formed on a first side of the base layer, and wherein the base layer comprises a first aperture,
the first aperture is adapted to provide access to a first tracking device,
the first tracking device is disposed within the first aperture, wherein the first tracking device comprises a coil, and
a first trace of the plurality of traces bends around a portion of the first aperture, and
an insulative layer formed over the traces to isolate the plurality of traces from an external environment; and
a malleable elongated tubular body,
wherein
the flexible circuit assembly is configured to be coupled to a non-planar surface of a flexible component of the malleable elongated tubular body, the base layer and the insulative layer include material properties combined with an overall thickness of the flexible circuit assembly that facilitate the flexible circuit assembly being flexible to conform to the non-planar surface and bend or flex with bending of the flexible component,
a first sensor wire and a second sensor wire extend from the first tracking device,
the first sensor wire is connected to a first pad of the first plurality of pads, and
the second sensor wire is connected to a second pad of the first plurality of pads.

20. The navigated medical instrument of claim 19, wherein the flexible circuit assembly is adhered to the malleable elongated tubular body.

21. The navigated medical instrument of claim 20, wherein:
the base layer comprises a second aperture;
the first tracking device includes a first coil;
the second aperture is adapted to provide access to a second tracking device;
the second tracking device comprises a second coil;
a portion of the second tracking device is disposed within the second aperture; and
a second trace of the plurality of traces bends around a portion of the second aperture.

22. The navigated medical instrument of claim 20, wherein the flexible circuit assembly is configured to flex three-dimensionally.

23. The navigated medical instrument of claim 20 comprises:
a first lead wire; and
a second lead wire,
wherein
the first lead wire and the second lead wire are configured to be coupled to the second plurality of pads,
each of the first sensor wire and the second sensor wire has an outer diameter of 0.01 mm,
each of the first lead wire and the second lead wire has an outer diameter of 0.05 mm, and
each of the first plurality of pads and the second plurality of pads has a width of 0.1-0.5 mm.

24. The navigated medical instrument of claim 23, wherein:
each of the first sensor wire, the second sensor wire, the first lead wire, and the second lead wire has an outer diameter of 0.01 mm; and
each of the first plurality of pads and the second plurality of pads has a width of 0.1 mm.

25. The navigated medical instrument of claim 19, wherein:
- an overall thickness of the flexible circuit assembly is 0.05 mm; and
- a corresponding bend radius of the flexible circuit assembly is 0.5 mm.

26. The navigated medical instrument of claim 19, wherein:
- the base layer comprises a second aperture;
- the second aperture is adapted to provide access to a second tracking device;
- the second tracking device is disposed within the second aperture; and
- the first trace and a second trace of the plurality of traces bend around a portion of the second aperture.

* * * * *

UNITED STATES PATENT AND TRADEMARK OFFICE
CERTIFICATE OF CORRECTION

| | | |
|---|---|---|
| PATENT NO. | : 9,226,688 B2 | Page 1 of 1 |
| APPLICATION NO. | : 13/748150 | |
| DATED | : January 5, 2016 | |
| INVENTOR(S) | : Brad Jacobsen et al. | |

It is certified that error appears in the above-identified patent and that said Letters Patent is hereby corrected as shown below:

Title page, (*) Notice: line 3, after "days.", insert --This patent is subject to a terminal disclaimer.--

Signed and Sealed this
Nineteenth Day of April, 2016

Michelle K. Lee
*Director of the United States Patent and Trademark Office*